United States Patent
Dickens et al.

(10) Patent No.: US 11,446,457 B2
(45) Date of Patent: Sep. 20, 2022

(54) METHODS AND APPARATUS FOR TREATING A RESPIRATORY DISORDER

(71) Applicants: ResMed Pty Ltd, Bella Vista (AU); ResMed Paris SAS, Moissy Cramayel (FR)

(72) Inventors: Paul Andrew Dickens, Sydney (AU); Dion Charles Chewe Martin, Sydney (AU); Olivier Tessier, Paris (FR); Peter Wlodarczyk, Ashfield (AU)

(73) Assignees: ResMed Pty Ltd; RESMED PARIS SAS

( * ) Notice: Subject to any disclaimer, the term of this patent is extended or adjusted under 35 U.S.C. 154(b) by 282 days.

(21) Appl. No.: 16/641,080

(22) PCT Filed: Aug. 24, 2018

(86) PCT No.: PCT/AU2018/050904
§ 371 (c)(1),
(2) Date: Feb. 21, 2020

(87) PCT Pub. No.: WO2019/036768
PCT Pub. Date: Feb. 28, 2019

(65) Prior Publication Data
US 2021/0187222 A1 Jun. 24, 2021

(30) Foreign Application Priority Data
Aug. 25, 2017 (AU) ................ 2017903443

(51) Int. Cl.
*A61M 16/00* (2006.01)
*A61B 5/00* (2006.01)
(Continued)

(52) U.S. Cl.
CPC ...... *A61M 16/024* (2017.08); *A61M 16/0057* (2013.01); *A61M 16/101* (2014.02);
(Continued)

(58) Field of Classification Search
USPC ............... 96/109, 115, 116, 121, 130, 96; 128/204.21, 204.23
See application file for complete search history.

(56) References Cited

U.S. PATENT DOCUMENTS 8,668,767 B2 * 3/2014 Sprinkle .............. A61M 16/105
128/205.12
2006/0230931 A1 10/2006 Bliss
(Continued)

FOREIGN PATENT DOCUMENTS

JP 2007512048 A 5/2007
JP 2012508074 A 4/2012
(Continued)

OTHER PUBLICATIONS

The Extended European Search Report for European Patent Application No. 18848780.5, dated Apr. 19, 2021.
(Continued)

*Primary Examiner* — Frank M Lawrence, Jr.
(74) *Attorney, Agent, or Firm* — Botos Churchill IP Law LLP

(57) ABSTRACT

An oxygen concentrator (100) apparatus and a method thereof implement operations control to efficiently release oxygen enriched gas to reduce potential waste. The control methodology may include generating a profile such as a minimum inhalation flow profile of the user. The profile may be based on a size parameter of the user. The method may determine one or more control parameters characterizing a bolus of oxygen enriched gas based on the generated flow profile. The control methodology may then generate a bolus release control signal, such as for a supply valve, according to the determined one or more control parameters. The
(Continued)

oxygen concentrator may then, with the control signal, release and deliver a bolus of oxygen enriched gas for a user such as for reducing waste.

30 Claims, 12 Drawing Sheets

(51) Int. Cl.
    *B01D 53/047* (2006.01)
    *A61M 16/10* (2006.01)
    *B01D 53/04* (2006.01)
    *A61M 16/20* (2006.01)

(52) U.S. Cl.
    CPC ....... *B01D 53/047* (2013.01); *B01D 53/0423* (2013.01); *A61M 16/105* (2013.01); *A61M 16/203* (2014.02); *A61M 2202/0208* (2013.01); *A61M 2205/42* (2013.01); *A61M 2205/8212* (2013.01); *A61M 2230/42* (2013.01); *A61M 2240/00* (2013.01); *B01D 2253/108* (2013.01); *B01D 2256/12* (2013.01); *B01D 2257/102* (2013.01); *B01D 2259/402* (2013.01); *B01D 2259/4533* (2013.01); *B01D 2259/4541* (2013.01)

(56) References Cited

U.S. PATENT DOCUMENTS

| | | | |
|---|---|---|---|
| 2007/0227360 A1* | 10/2007 | Atlas | A61M 16/101 96/121 |
| 2010/0051030 A1 | 3/2010 | Richard et al. | |
| 2012/0055477 A1 | 3/2012 | Wilkinson | |
| 2014/0137744 A1 | 5/2014 | Wilkinson et al. | |
| 2014/0261424 A1 | 9/2014 | Doyle et al. | |
| 2016/0206837 A1 | 7/2016 | Dong et al. | |
| 2018/0243528 A1* | 8/2018 | Zapol | A61M 16/0666 |

FOREIGN PATENT DOCUMENTS

| | | |
|---|---|---|
| JP | 2015531308 A | 11/2015 |
| WO | 2009105597 A1 | 9/2009 |
| WO | 2014059405 A1 | 4/2014 |
| WO | 2014059408 A1 | 4/2014 |
| WO | 2017096428 A1 | 6/2017 |

OTHER PUBLICATIONS

International Search Report issued in corresponding AU application No. PCT/AU2018/050904 dated Dec. 17, 2018.
Respiratory Physiology: Physiology of the Airway published on 2013. [retrieved from the internet Oct. 29, 2018] <https://www.sciencedirect.com/topics/neuroscience/respiratory-physiology> A entire document.
"Merck Manual: Overview of Mechanical Ventilation [retrieved from the internet Oct. 29, 2018]", <https://web.archive.org/web/20170220083405/www.merckmanuals.com/en-pr/professional/critical-care-medicine/respiratory-failure-and-mechanical-ventilation/overview-of-mechanical-ventilation>, Feb. 20, 2017.
Notice of Reasons for Rejection for Japanese Patent Application No. 2020-511533, dated Apr. 22, 2022.

* cited by examiner

METHODS AND APPARATUS FOR TREATING A RESPIRATORY DISORDER

CROSS-REFERENCE TO RELATED APPLICATIONS

The present application is a national phase entry under 35 U.S.C. § 371 of International Application No. PCT/AU2018/050904 filed Aug. 24, 2018, published in English, which claims priority from Australian Provisional Patent Application No. 2017903443 filed Aug. 25, 2017, all of the disclosure of which are incorporated herein by reference.

FIELD OF THE TECHNOLOGY

The present technology relates generally to methods and apparatus for treating respiratory disorders, such as an oxygen concentrator. In some examples, the technology more specifically concerns methods and apparatus for increasing the efficiency of an oxygen concentrator such as with pulsed oxygen delivery.

DESCRIPTION OF THE RELATED ART

There are many users that require supplemental oxygen as part of Long Term Oxygen Therapy (LTOT). Currently, the vast majority of users that are receiving LTOT are diagnosed under the general category of Chronic Obstructive Pulmonary Disease (COPD). This general diagnosis includes such common diseases as Chronic Asthma, Emphysema, and several other cardio-pulmonary conditions. Other users may also require supplemental oxygen, for example, obese individuals to maintain elevated activity levels, or infants with cystic fibrosis or broncho-pulmonary dysplasia.

Doctors may prescribe oxygen concentrators or portable tanks of medical oxygen for these users. Usually a specific continuous oxygen flow rate is prescribed (e.g., 1 litre per minute (LPM), 2 LPM, 3 LPM, etc.). Experts in this field have also recognized that exercise for these users provides long term benefits that slow the progression of the disease, improve quality of life and extend user longevity. Most stationary forms of exercise like tread mills and stationary bicycles, however, are too strenuous for these users. As a result, the need for mobility has long been recognized. Until recently, this mobility has been facilitated by the use of small compressed oxygen tanks. The disadvantage of these tanks is that they have a finite amount of oxygen and they are heavy, weighing about 50 pounds, when mounted on a cart with dolly wheels.

Oxygen concentrators have been in use for about 50 years to supply users suffering from respiratory insufficiency with supplemental oxygen. Traditional oxygen concentrators used to provide these flow rates have been bulky and heavy making ordinary ambulatory activities with them difficult and impractical. Recently, companies that manufacture large stationary home oxygen concentrators began developing portable oxygen concentrators (POCs). The advantage of POCs is that they can produce a theoretically endless supply of oxygen. In order to make these devices small for mobility, the various systems necessary for the production of oxygen enriched gas are condensed.

Portable oxygen concentrators seek to utilize their produced oxygen as efficiently as possible, in order to minimise weight, size, and power consumption. This may be achieved by delivering oxygen as a bolus timed to coincide with a detection of the start of user inspiration, in a mode known as pulsed or demand (oxygen) delivery. This approach preserves accumulated oxygen by minimizing or avoiding oxygen release during user expiration.

There is therefore a need to improve pulsed oxygen delivery (POD) such as to reduce waste of delivered oxygen for a given user. It may also be beneficial if improvements to the device broadened its use for a larger range of potential users, extending from adult to neonate.

SUMMARY

Methods and apparatus for treating a respiratory disorder as described herein may be implemented with improved control of pulsed oxygen delivery, such as by controlling an electro-mechanical valve(s) governing oxygen enriched gas release from a storage vessel. Such devices may implement greater control over release of accumulated oxygen so as to permit beneficial oxygen delivery for the user while using less oxygen by minimizing potential oxygen waste. Such improvement may occur even during user inspiration. For example, for a given user, a "delivery envelope" representing constraints for a release of oxygen over a time period such as during a breath or inspiratory portion of breath, may be estimated based on certain user measurements and device settings. The delivery envelope may be defined as the region within which the parameters of the bolus may be set so as to eliminate retrograde flow waste and/or anatomic deadspace waste of oxygen enriched gas for that user.

Furthermore, the bolus parameters may be varied within the delivery envelope so as to determine and deliver the optimal bolus parameters for a given user, i.e. those parameters that maximise the therapeutic effect of pulsed oxygen delivery for that user, or equivalently, minimise physiologic deadspace waste. The determination may be subjective, based on user feedback, and/or objective, based on sensor data.

Some versions of the present technology may include a method of controlling oxygen enriched gas release with a controller of an oxygen concentrator. The method may include generating a minimum inhalation flow profile of a user based on a size parameter of the user. The method may include determining one or more control parameters characterizing a bolus of oxygen enriched gas based on the generated minimum inhalation flow profile. The method may include generating, with the controller, a bolus release control signal for controlling release of a bolus of oxygen enriched gas according to the determined one or more control parameters.

In some versions, the method may further include calculating an alveolar time for the user based on the minimum inhalation flow profile, wherein the one or more control parameters are further based on the calculated alveolar time. The method may further include deriving a delivery envelope for the one or more control parameters from the minimum inhalation flow profile, and may further include constraining the one or more control parameters within the delivery envelope. The method may further include calculating an alveolar time for the user based on the minimum inhalation flow profile, wherein the delivery envelope may be further based on the calculated alveolar time. The size parameter of the user may be height such that the method may further include estimating an anatomic deadspace of the user from the height, wherein the alveolar time may be further based on the estimated anatomic deadspace.

In some versions, the method may further include generating one or more sensor signals representing properties of the oxygen concentrator or the user. The method may further estimating an inspiratory time of the user from the one or more sensor signals. The minimum inhalation flow profile may be further based on the estimated inspiratory time. The method may include determining a volume for the bolus based on a setting of the oxygen concentrator, wherein the one or more control parameters may be further based on the determined volume for the bolus. The determining the volume for the bolus may be further based on a breathing rate of the user. The method may further include estimating the breathing rate of the user from one or more sensor signals representing properties of the oxygen concentrator or the user. The determining the one or more control parameters may include any or all of: setting an onset delay that may be less than an inspiratory time of the minimum inhalation flow profile; setting a bolus amplitude profile to correspond with the minimum inhalation flow profile between the onset delay and a bolus duration; and computing the bolus duration based on the bolus amplitude profile and the determined volume for the bolus. The determining the one or more control parameters may include any or all of: setting an onset delay that may be less than an inspiratory time of the minimum inhalation flow profile; setting a bolus amplitude profile to be equal to a value of the minimum inhalation flow profile at the onset delay over a range from the onset delay to a bolus duration; and computing the bolus duration based on the bolus amplitude profile and the determined volume for the bolus.

In some versions, the method may further include calculating an alveolar time for the user based on the minimum inhalation flow profile, wherein the onset delay may be less than the calculated alveolar time. The size parameter may be a height of the user such that the method may further include estimating an anatomic deadspace of the user from the height of the user, wherein the calculated alveolar time may be further based on the estimated anatomic deadspace. The determining the one or more control parameters may include any or all of: setting a bolus duration that may be less than an inspiratory time of the minimum inhalation flow profile; setting a bolus amplitude profile to follow the minimum inhalation flow profile between an onset delay and the bolus duration; and computing the onset delay based on the bolus amplitude profile and the determined volume for the bolus. The determining the one or more control parameters may include any or all of: setting a bolus duration that may be less than an inspiratory time of the minimum inhalation flow profile; setting a bolus amplitude profile to be equal to a value of the minimum inhalation flow profile at an onset delay over a range from the onset delay to the bolus duration; and computing the onset delay based on the bolus amplitude profile and the determined volume for the bolus. The method may further include calculating an alveolar time for the user based on the minimum inhalation flow profile, wherein the bolus duration may be less than the alveolar time. The size parameter may be a height of the user such that the method may further include estimating an anatomic deadspace of the user from the height of the user, wherein the alveolar time may be further based on the anatomic deadspace.

In some versions, the method may further include any or all of: estimating a beneficial effect of a bolus delivered in accordance with the bolus release control signal; determining one or more further control parameters characterizing an additional bolus of oxygen enriched gas based on the minimum inhalation flow profile and the estimated beneficial effect; and generating, with the controller, a further bolus release control signal according to the determined one or more further control parameters.

In some versions, the method may further include receiving, in the controller, a boost signal from an input interface of the oxygen concentrator, and in response thereto, controlling, by the controller of the oxygen concentrator, release of one or more boost boluses, wherein a total volume of oxygen enriched gas of a released bolus of the one or more boost boluses includes (1) an equivalent volume that satisfies a continuous-flow-rate setting of the oxygen concentrator as set at the input interface plus (2) an additional volume quantity of oxygen enriched gas. The controller may discontinue release of the additional volume quantity of oxygen enriched gas after a predetermined time or in response to a further signal from the input interface of the oxygen concentrator. The determining the one or more control parameters may include calculating the control parameters to reduce one or more of retrograde flow waste, anatomic deadspace waste and physiologic deadspace waste. The method may further include releasing a bolus of oxygen enriched gas in accordance with the bolus release control signal for delivery to the user via a delivery device, whereby the delivered bolus reduces one or more of retrograde flow waste, anatomic deadspace waste and physiologic deadspace waste.

Some versions of the present technology may include an oxygen concentrator apparatus. The oxygen concentrator apparatus may include at least two canisters. The oxygen concentrator apparatus may include gas separation adsorbent disposed in the at least two canisters, wherein the gas separation adsorbent separates at least some nitrogen from air in the at least two canisters to produce oxygen enriched gas. The oxygen concentrator apparatus may include a compression system. The compression system may include a compressor coupled to at least one of the canisters, wherein the compressor compresses air during operation. The compression system may include a motor coupled to the compressor, wherein the motor drives operation of the compressor. The oxygen concentrator apparatus may include an accumulator coupled to one or more of the canisters, wherein oxygen enriched gas produced in one or more of the canisters may be passed into the accumulator during use. The oxygen concentrator apparatus may include a controller, including one or more processors, and a set of valves coupled to the controller. The controller may be configured to control operation of the set of valves such as to (a) produce oxygen enriched gas into the accumulator and/or (b) release the produced oxygen enriched gas from the accumulator in at least one bolus. The controller may be further configured to generate a minimum inhalation flow profile of a user based on a size parameter of the user. The controller may be further configured to determine one or more control parameters characterizing the at least one bolus based on the generated minimum inhalation flow profile. The controller may be further configured to generate a bolus release control signal according to the determined one or more control parameters, the generated bolus release control signal configured to cause the at least one bolus to be released from the accumulator.

In some versions, the oxygen concentrator apparatus may further include a control panel coupled to the controller and configured to receive the size parameter of the user via manual entry. The controller may include a carrier medium having processor control instructions that, when executed by the one or more processors, cause the oxygen concentrator apparatus to perform any on the methods described herein.

Some versions of the present technology may include a method of controlling oxygen enriched gas release with a controller of an oxygen concentrator in pulsed oxygen delivery mode. The method may include deriving a delivery envelope of parameters of a potential bolus of oxygen enriched gas based on a size parameter of a user. The method may include determining one or more control parameters characterizing a deliverable bolus of oxygen enriched gas so that the one or more control parameters may be constrained within the delivery envelope. The method may include generating, with the controller, a bolus release control signal for controlling release of a bolus of oxygen enriched gas according to the determined one or more control parameters. The method may further include calculating an alveolar time for the user based on the size parameter, wherein the deriving the delivery envelope may be further based on the calculated alveolar time. The method may further include generating a minimum inhalation flow profile for the user based on the size parameter, wherein the deriving the delivery envelope may be based on the minimum inhalation flow profile. The calculated alveolar time may be further based on the minimum inhalation flow profile. The size parameter of the user may be height such that the method may further include estimating an anatomic deadspace of the user from the height, wherein the calculated alveolar time may be further based on the estimated anatomic deadspace.

In some versions, the method may further include generating one or more sensor signals representing properties of the oxygen concentrator or the user. The method may further include estimating an inspiratory time of the user from the one or more sensor signals. The derived delivery envelope may be further based on the estimated inspiratory time. The method may further may include determining a volume for the potential bolus based on a setting of the oxygen concentrator, wherein the one or more control parameters may be further based on the determined bolus volume. The determining the bolus volume may be further based on a breathing rate of the user. The method may further include estimating the breathing rate of the user from one or more sensor signals representing properties of the oxygen concentrator or the user. The method may include any or all of estimating a beneficial effect of a bolus delivered in accordance with the bolus release control signal; determining one or more further control parameters characterizing an additional bolus of oxygen enriched gas based on the estimated beneficial effect, wherein the determined one or more further control parameters are constrained within the delivery envelope; and generating, with the controller, a further bolus release control signal according to the determined further control parameters.

In some versions, the method may include any or all of receiving, in the controller, a boost signal from an input interface of the oxygen concentrator, and in response thereto, controlling, by the controller of the oxygen concentrator, release of one or more boost boluses, wherein a total volume of oxygen enriched gas of a released boost bolus of the one or more boost boluses may include (1) an equivalent volume that satisfies a continuous-flow-rate setting of the oxygen concentrator as set at the input interface plus (2) an additional volume quantity of oxygen enriched gas. The controller may discontinue release of the additional volume quantity of oxygen enriched gas after a predetermined time or in response to a further signal from the input interface of the oxygen concentrator.

In some versions, the determining the one or more control parameters may include calculating the control parameters to reduce one or more of retrograde flow waste, anatomic deadspace waste and physiologic deadspace waste. The method may further include releasing a bolus of oxygen enriched gas in accordance with the bolus release control signal for delivery to the user via a delivery device, whereby the delivered bolus may reduce one or more of retrograde flow waste, anatomic deadspace waste and physiologic deadspace waste.

Some versions of the present technology may include an oxygen concentrator apparatus. The apparatus may include at least two canisters. The apparatus may include gas separation adsorbent disposed in the at least two canisters, wherein the gas separation adsorbent separates at least some nitrogen from air in the at least two canisters to produce oxygen enriched gas. The apparatus may include a compression system. The compression system may include a compressor coupled to at least one of the canisters, wherein the compressor compresses air during operation. The compression system may include a motor coupled to the compressor, wherein the motor drives operation of the compressor. The apparatus may include an accumulator coupled to one or more of the canisters, wherein oxygen enriched gas produced in one or more of the canisters may be passed into the accumulator during use. The apparatus may include a controller, including one or more processors. The apparatus may include a set of valves coupled to the controller. The controller may be configured to control operation of the set of valves to (a) produce oxygen enriched gas into the accumulator and/or (b) release, such as in pulsed oxygen delivery mode, the produced oxygen enriched gas from the accumulator in at least one bolus. The controller may be further configured to derive a delivery envelope of parameters of a potential bolus of oxygen enriched gas based on a size parameter of a user. The controller may be further configured to determine one or more control parameters characterizing a deliverable bolus of oxygen enriched gas so that the one or more parameters are constrained within the delivery envelope. The controller may be further configured to generate a bolus release control signal according to the determined one or more control parameters. The bolus release control signal may be for controlling release of a bolus of oxygen enriched gas from the accumulator.

In some versions, the apparatus may include a control panel coupled to the controller. The controller may be configured to receive the size parameter of the user via manual entry on the control panel. The controller may include a carrier medium having processor control instructions that, when executed by the one or more processors, cause the oxygen concentrator apparatus to perform any method described herein.

Some versions of the present technology may include a method of a processor for generating an inhalation flow profile for a user. The method may include estimating a tidal volume for the user based on a size parameter of the user and a breathing rate of the user. The method may include generating the inhalation flow profile for the user from the tidal volume and an inspiratory time for the user. The size parameter may be height, such that estimating the tidal volume may include estimating an alveolar minute ventilation for the user based on the height of the user. Estimating the tidal volume may further include estimating an anatomic deadspace for the user based on the height of the user. Estimating the tidal volume may include adding the anatomic deadspace to a ratio of the alveolar minute ventilation to the breathing rate of the user. Generating the inhalation flow profile may include calculating a peak inspiratory flow rate for the user from the tidal volume for the user, the inspiratory time, and a template function for the inhalation flow profile. The template function may be a sinusoidal half-wave. The method further may include estimating the inspiratory time from the size parameter. The method may further may include, with a controller of a respiratory therapy device, controlling a respiratory therapy based on the generated inhalation flow profile. The controlling the respiratory therapy may include controlling an oxygen concentrator based on the inhalation flow profile.

Some versions of the present technology may include an oxygen concentrator apparatus. The oxygen concentrator may include at least two canisters. The oxygen concentrator may include gas separation adsorbent disposed in the at least two canisters. The gas separation adsorbent serves to separate at least some nitrogen from air in the at least two canisters to produce oxygen enriched gas. The oxygen concentrator may include a compression system. The compression system may include a compressor coupled to at least one of the canisters, wherein the compressor compresses air during operation. The compression system may include a motor coupled to the compressor, wherein the motor drives operation of the compressor. The oxygen concentrator may include an accumulator coupled to one or more of the canisters, wherein oxygen enriched gas produced in one or more of the canisters may be passed into the accumulator during use. The oxygen concentrator may include a controller, including one or more processors. The oxygen concentrator may include a set of valves coupled to the controller. The controller may be configured to control operation of the set of valves to (a) produce oxygen enriched gas into the accumulator and/or (b) release the produced oxygen enriched gas from the accumulator. The controller may be further configured to estimate a tidal volume for a user based on a size parameter of the user and a breathing rate of the user. The controller may be further configured to generate an inhalation flow profile for the user from the tidal volume and an inspiratory time for the user.

In some versions, the controller may include a carrier medium having processor control instructions that, when executed by the one or more processors, cause the oxygen concentrator apparatus to perform any of the methods described herein.

Some versions of the present technology may include a method of a controller for controlling a respiratory therapy device. The method may include estimating a resting energy expenditure of a user based on a size parameter of the user. The method may include estimating a respiratory parameter for the user based on the estimated resting energy expenditure. The method may include controlling the respiratory therapy device based on the estimated respiratory parameter.

In some versions, the respiratory parameter may be tidal volume such that the estimating the respiratory parameter may include any or all of: computing an alveolar minute ventilation based on the estimated resting energy expenditure, and estimating a tidal volume based on the computed alveolar minute ventilation and a breathing rate for the user. The estimating the tidal volume may account for an activity state of the user to provide a minimum or elevated estimate of the tidal volume. The respiratory therapy device may be a ventilator, wherein the estimated tidal volume may be a minimum tidal volume estimate, and wherein the controlling the respiratory therapy device may include initialising low tidal volume alarms based on the minimum tidal volume estimate. The respiratory therapy device may be a ventilator, wherein the estimated tidal volume may be an elevated tidal volume estimate, and wherein the controlling the respiratory therapy device may include initialising high tidal volume alarms based on the elevated tidal volume estimate. The respiratory therapy device may be a ventilator, wherein the estimated tidal volume may be a minimum tidal volume estimate, and wherein the controlling the respiratory therapy device may include initialising a tidal volume for volume control modes based on the minimum tidal volume estimate. The estimating the tidal volume may account for a pathology of the user to provide a typical estimate of the tidal volume for the pathology. The respiratory therapy device may be a ventilator, wherein the estimated tidal volume may be a typical tidal volume estimate for the pathology, and wherein the controlling the respiratory therapy device may include initialising target tidal volume settings for volume assurance modes using the typical tidal volume estimate.

In some versions, the respiratory parameter may be minute ventilation such that the estimating the minimum respiratory parameter may include any or all of: computing an alveolar minute ventilation based on the resting energy expenditure, and estimating a minute ventilation based on the computed alveolar minute ventilation and an estimate of an anatomic deadspace for the user obtained from the size parameter. The estimating the minute ventilation may account for an activity state of the user to provide a minimum or elevated estimate of the minute ventilation.

In some versions, the respiratory therapy device may be a ventilator, wherein the estimated minute ventilation may be a minimum minute ventilation estimate, and wherein the controlling the respiratory therapy device may include initialising low minute ventilation alarms based on the minimum minute ventilation estimate. The respiratory therapy device may be a ventilator, wherein the estimated minute ventilation may be an elevated minute ventilation estimate, and wherein the controlling the respiratory therapy device may include initialising high minute ventilation alarms based on the elevated minute ventilation estimate. The respiratory therapy device may be an oxygen concentrator such that the controlling the respiratory therapy device may include any or all of: generating a minimum inhalation flow profile for the user from the estimated respiratory parameter; determining one or more control parameters for a bolus of oxygen enriched gas produced by the oxygen concentrator based on the generated minimum inhalation flow profile; and generating a bolus release control signal for controlling release of a bolus of oxygen enriched gas according to the determined one or more control parameters.

Some versions of the present technology include a respiratory therapy apparatus. The apparatus may include a controller, including one or more processors. The controller may be configured to control one or more operations of the respiratory therapy apparatus to produce a respiratory therapy. The controller may be configured to estimate a resting energy expenditure of a user based on a size parameter of the user. The controller may be configured to estimate a respiratory parameter for the user based on the estimated resting energy expenditure. The controller may be configured to control an operation of the respiratory therapy apparatus based on the estimated respiratory parameter.

In some versions, the controller may include a carrier medium having processor control instructions that, when executed by the one or more processors, cause the respiratory therapy apparatus to perform any of the methods described herein.

Some versions of the present technology may include a method of controlling oxygen enriched gas release with a controller of an oxygen concentrator in pulsed oxygen delivery mode. The method may include determining one or more control parameters characterizing a deliverable bolus of oxygen enriched gas. The method may include generating, with the controller, a bolus release control signal for controlling release of a bolus of oxygen enriched gas according to the determined one or more control parameters. The method may include receiving, in the controller, a boost signal from an input interface of the oxygen concentrator. The method may include, in response to the boost signal, controlling one or more further bolus release control signals for controlling release of one or more boost boluses, wherein a total volume of oxygen enriched gas of a released bolus of the one or more boost boluses includes: (1) an equivalent volume that satisfies a continuous-flow-rate setting of the oxygen concentrator as set at the input interface plus (2) an additional volume quantity of oxygen enriched gas.

In some versions, the method may include discontinuing, by the controller, release of the additional volume quantity of oxygen enriched gas after a predetermined time or in response to receiving, in the controller, a further signal from the input interface of the oxygen concentrator.

Some versions of the present technology may include an oxygen concentrator apparatus. The oxygen concentrator apparatus may include at least two canisters. The oxygen concentrator apparatus may include gas separation adsorbent disposed in the at least two canisters, wherein the gas separation adsorbent separates at least some nitrogen from air in the at least two canisters to produce oxygen enriched gas. The oxygen concentrator apparatus may include a compression system including a compressor coupled to at least one of the canisters, wherein the compressor compresses air during operation; and a motor coupled to the compressor, wherein the motor drives operation of the compressor. The oxygen concentrator apparatus may include an accumulator coupled to one or more of the canisters, wherein oxygen enriched gas produced in one or more of the canisters may be passed into the accumulator during use. The oxygen concentrator apparatus may include a controller, including one or more processors, and a set of valves coupled to the controller. The controller may be configured to control operation of the set of valves to (a) produce oxygen enriched gas into the accumulator and/or (b) release the produced oxygen enriched gas from the accumulator. The controller may be further configured to determine one or more control parameters characterizing a deliverable bolus of oxygen enriched gas. The controller may be further configured to generate a bolus release control signal for controlling release of a bolus of oxygen enriched gas according to the determined one or more control parameters. The controller may be further configured to receive a boost signal from an input interface of the oxygen concentrator apparatus. The controller may be further configured to, in response to the boost signal, control one or more further bolus release control signals for controlling release of one or more boost boluses, wherein a total volume of oxygen enriched gas of a released bolus of the one or more boost boluses includes: (1) an equivalent volume that satisfies a continuous-flow-rate setting of the oxygen concentrator apparatus as set at the input interface plus (2) an additional volume quantity of oxygen enriched gas.

In some versions, the controller may be configured to discontinue release of the additional volume quantity of oxygen enriched gas after a predetermined time or in response to receiving a further signal from the input interface of the oxygen concentrator apparatus.

The methods described herein can, in part, provide improved functioning in a controller or processor, such as of a controller or processor of a portable oxygen concentrator. Moreover, the methods/systems, devices/apparatus can provide improvements in the technological field of automated monitoring and/or treatment of respiratory disorders, including, for example, operations of portable oxygen concentrators.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE DRAWINGS

Advantages of the present technology will become apparent to those skilled in the art with the benefit of the following detailed description of embodiments and upon reference to the accompanying drawings in which like reference numerals refer to similar elements.

Figure 1:
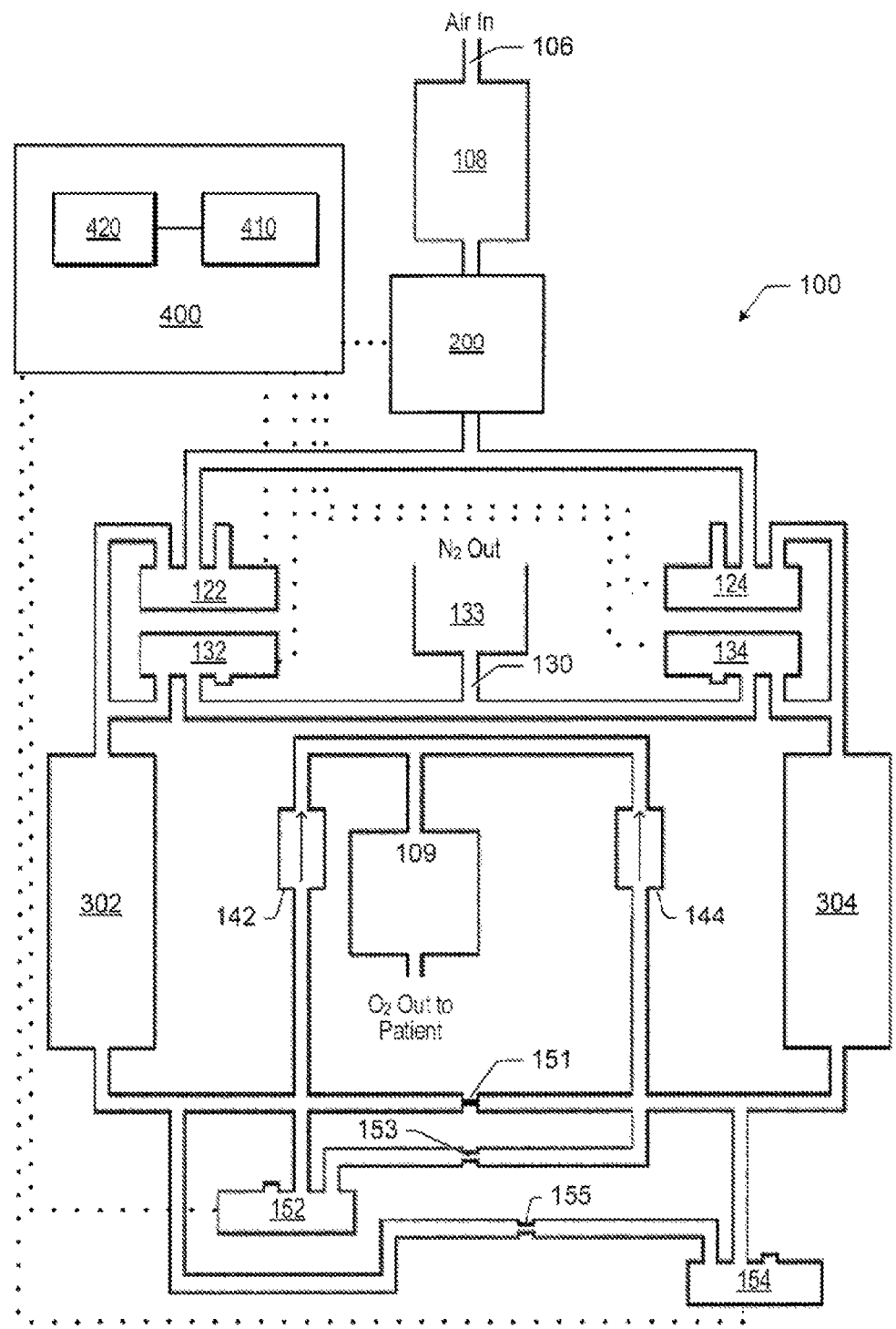
FIG. 1 is a schematic diagram of the components of an example oxygen concentrator.

While the technology may be implemented with various modifications and alternative forms, specific embodiments thereof are shown by way of example in the drawings and are described in detail herein. It should be understood, however, that the drawings and detailed description thereto are not intended to limit the technology to the particular form disclosed. Various modifications, equivalents, and alternatives may be implemented by combining any of the disclosed features of any of the specific examples described.

DETAILED DESCRIPTION OF THE EMBODIMENTS

The present technology may be understood in accordance with the terminology used herein. Headings are for organizational purposes only and are not meant to be used to limit or interpret the description or claims. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to."

The term "coupled" as used herein means either a direct connection or an indirect connection (e.g., one or more intervening connections) between one or more objects or components. The phrase "connected" means a direct connection between objects or components such that the objects or components are connected directly to each other. As used herein the phrase "obtaining" a device means that the device is either purchased or constructed.

Oxygen concentrators take advantage of pressure swing adsorption (PSA). Pressure swing adsorption may involve using a compressor to increase gas pressure inside a canister that contains particles of a gas separation adsorbent. As the pressure increases, certain molecules in the gas may become adsorbed onto the gas separation adsorbent. Removal of a portion of the gas in the canister under the pressurized conditions allows separation of the nonadsorbed molecules from the adsorbed molecules. The gas separation adsorbent may be regenerated by reducing the pressure, which reverses the adsorption of molecules from the adsorbent. Further details regarding oxygen concentrators may be found, for example, in U.S. Published Patent Application No. 2009-0065007, published Mar. 12, 2009, and entitled "Oxygen Concentrator Apparatus and Method", which is incorporated herein by reference.

Ambient air usually includes approximately 78% nitrogen and 21% oxygen with the balance comprised of argon, carbon dioxide, water vapor and other trace gases. If a gas mixture such as air, for example, is passed under pressure through a vessel containing a gas separation adsorbent bed that attracts nitrogen more strongly than it does oxygen, part or all of the nitrogen will stay in the bed, and the gas coming out of the vessel will be enriched in oxygen. When the bed reaches the end of its capacity to adsorb nitrogen, it can be regenerated by reducing the pressure, thereby releasing the adsorbed nitrogen. It is then ready for another cycle of producing oxygen enriched gas. By alternating canisters in a two-canister system, one canister can be collecting oxygen while the other canister is being purged (resulting in a continuous separation of the oxygen from the nitrogen). In this manner, oxygen can be accumulated, such as in a storage container or other pressurizable vessel or conduit coupled to the canisters, from the ambient air for a variety of uses include providing supplemental oxygen to users.

As previously noted, delivery of the accumulated oxygen, such as from a storage container or accumulator, as a bolus timed to coincide with the start of inspiration in a mode known as pulsed or demand (oxygen) delivery may help to conserve the produced/accumulated oxygen. This approach, while avoiding the waste of delivering oxygen during expiration, still has the potential to waste oxygen, in at least the following three ways:

(1) Any portion of the bolus whose flow rate exceeds the instantaneous inspiratory flow rate may not be inspired during the current breath. For example, some of this portion may flow back out of the user's nostrils (retrograde flow) to atmosphere, where it may pool around the airway opening for subsequent inhalation, but more likely be wasted to atmosphere. Pooling of delivered oxygen may potentially occur within the user's airways to be inhaled in the subsequent breath(s), such as during mouth breathing, or if a bolus is delivered during the pause before the start of inspiration. However, pooling is often unpredictable, so the conservative pulsed oxygen delivery assumption is that that any portion of a bolus whose flow rate exceeds the instantaneous inspiratory flow rate is wasted. This type of oxygen waste may be considered to be "retrograde flow waste."

(2) Due to the nature of mammalian respiration—that of tidal breathing with conduit airways to an internal lung—not all of the inspiratory flow reaches the gas-exchanging areas of the lung; the end portion of each inspiration remains in the conduit airways (i.e., the anatomic deadspace) and is exhaled without reaching the alveoli. Therefore, oxygen delivered during the later part of inspiration will only reach the anatomic deadspace. This type of oxygen waste may be considered to be "anatomic deadspace waste."

(3) In COPD users, the lung can be relatively heterogeneous, in that some groups of alveoli are not perfused by blood and therefore form "physiologic deadspace". Portions of the bolus that reach such non-functioning alveoli are also wasted. This type of oxygen waste may be considered to be "physiologic deadspace waste."

Examples of the present technology may be implemented to reduce or minimize any or all of these potential oxygen waste types.

For example, FIG. 1 illustrates a schematic diagram of an example oxygen concentrator 100, that may be implemented with the present technology. Oxygen concentrator 100 may concentrate oxygen out of an air stream to provide oxygen enriched gas to a user. As used herein, "oxygen enriched gas" is composed of at least about 50% oxygen, at least about 60% oxygen, at least about 70% oxygen, at least about 80% oxygen, at least about 90% oxygen, at least about 95% oxygen, at least about 98% oxygen, or at least about 99% oxygen.

Oxygen concentrator 100 may be a portable oxygen concentrator. For example, oxygen concentrator 100 may have a weight and size that allows the oxygen concentrator to be readily carried or supported by hand and/or in a carrying case, such as by a user of the oxygen concentrator. In one embodiment, oxygen concentrator 100 has a weight of less than about 20 lbs., less than about 15 lbs., less than about 10 lbs, or less than about 5 lbs. In an embodiment, oxygen concentrator 100 has a volume of less than about 1000 cubic inches, less than about 750 cubic inches; less than about 500 cubic inches, less than about 250 cubic inches, or less than about 200 cubic inches.

Oxygen may be collected from ambient air by pressurising ambient air in canisters 302 and 304, which include a gas separation adsorbent. Gas separation adsorbents useful in an oxygen concentrator are capable of separating at least nitrogen from an air stream to produce oxygen enriched gas. Examples of gas separation adsorbents include molecular sieves that are capable of separation of nitrogen from an air stream. Examples of adsorbents that may be used in an oxygen concentrator include, but are not limited to, zeolites (natural) or synthetic crystalline aluminosilicates that separate nitrogen from oxygen in an air stream under elevated pressure. Examples of synthetic crystalline aluminosilicates that may be used include, but are not limited to: OXYSIV adsorbents available from UOP LLC, Des Plaines, Iowa; SYLOBEAD adsorbents available from W. R. Grace & Co, Columbia, Md.; SILIPORITE adsorbents available from CECA S.A. of Paris, France; ZEOCHEM adsorbents available from Zeochem AG, Uetikon, Switzerland; and AgLi-LSX adsorbent available from Air Products and Chemicals, Inc., Allentown, Pa.

As shown in FIG. 1, air may enter the oxygen concentrator through air inlet 106. Air may be drawn into air inlet 106 by compression system 200. Compression system 200 may draw in air from the surroundings of the oxygen concentrator and compress the air, forcing the compressed air into one or both canisters 302 and 304. In an embodiment, an inlet muffler 108 may be coupled to air inlet 106 to reduce sound produced by air being pulled into the oxygen concentrator by compression system 200. In an embodiment, inlet muffler 108 may be a moisture and sound absorbing muffler. For example, a water absorbent material (such as a polymer water absorbent material or a zeolite material) may be used to both remove or reduce water from the incoming air and to reduce the sound of the air passing into the air inlet 106.

Compression system 200 may include one or more compressors capable of compressing air. Pressurized air, produced by compression system 200, may be forced into one or both of the canisters 302 and 304. In some embodiments, the ambient air may be pressurized in the canisters to a pressure approximately in a range of 13-20 pounds per square inch (psi). Other pressures may also be used, depending on the type of gas separation adsorbent disposed in the canisters.

Coupled to each canister 302/304 are inlet valves 122/124 and outlet valves 132/134. As shown in FIG. 1, inlet valve 122 is coupled to canister 302 and inlet valve 124 is coupled to canister 304. Outlet valve 132 is coupled to canister 302 and outlet valve 134 is coupled to canister 304. Inlet valves 122/124 are used to control or gate the passage of air from compression system 200 to the respective canisters. Outlet valves 132/134 are used to release or gate gas from the respective canisters during a venting process. In some embodiments, inlet valves 122/124 and outlet valves 132/134 may be silicon plunger solenoid valves. Other types of valves, however, may be used. Plunger valves offer advantages over other kinds of valves by being quiet and having low slippage.

In some embodiments, a two-step valve actuation voltage may be used to control inlet valves 122/124 and outlet valves 132/134. For example, a high voltage (e.g., 24 V) may be applied to an inlet valve to open the inlet valve. The voltage may then be reduced (e.g., to 7 V) to keep the inlet valve open. Using less voltage to keep a valve open may use less power (Power=Voltage*Current). This reduction in voltage minimizes heat buildup and power consumption to extend run time from the battery. When the power is cut off to the valve, it closes by spring action. In some embodiments, the voltage may be applied as a function of time that is not necessarily a stepped response (e.g., a curved downward voltage between an initial 24 V and a final 7 V).

In an embodiment, pressurized air is sent into one of canisters 302 or 304 while the other canister is being vented. For example, during use, inlet valve 122 is opened while inlet valve 124 is closed. Pressurized air from compression system 200 is forced into canister 302, while being inhibited from entering canister 304 by inlet valve 124. In an embodiment, a controller 400 is electrically coupled to valves 122, 124, 132, and 134. Controller 400 includes one or more processors 410 operable to execute program instructions stored in memory 420. The program instructions are operable to perform various predefined methods that are used to control operation of the oxygen concentrator. Such operations are described in more detail herein. Thus, controller 400 may include program instructions for controlling a generation of valve control signals that control operations of the valves 122, 124, 132 and 134. For example, controller 400 may include program instructions for operating inlet valves 122 and 124 out of phase with each other, i.e., when one of inlet valves 122 or 124 is opened, the other valve is closed. During pressurization of canister 302, outlet valve 132 is closed and outlet valve 134 is opened. Similar to the inlet valves, controller 400 may include program instructions for operating outlet valves 132 and 134 such that they are operated out of phase with each other. In some embodiments, the voltages and the duration of the voltages of the signals used to open the input and output valves may be controlled by controller 400.

Check valves 142 and 144 are coupled to canisters 302 and 304, respectively. Check valves 142 and 144 are one-way valves that are passively operated by the pressure differentials that occur as the canisters are pressurized and vented. Check valves 142 and 144 are coupled to canisters to allow oxygen produced during pressurization of the canister to flow out of the canister, and to inhibit back flow of oxygen or any other gases into the canister. In this manner, check valves 142 and 144 act as one-way valves allowing oxygen enriched gas to exit the respective canister during pressurization.

The term "check valve", as used herein, refers to a valve that allows flow of a fluid (gas or liquid) in one direction and inhibits back flow of the fluid. Examples of check valves that are suitable for use include, but are not limited to: a ball check valve; a diaphragm check valve; a butterfly check valve; a swing check valve; a duckbill valve; and a lift check valve. Under pressure, nitrogen molecules in the pressurized ambient air are adsorbed by the gas separation adsorbent in the pressurized canister. As the pressure increases, more nitrogen is adsorbed until the gas in the canister is enriched in oxygen. The nonadsorbed gas molecules (mainly oxygen) flow out of the pressurized canister when the pressure reaches a point sufficient to overcome the resistance of the check valve coupled to the canister. In one embodiment, the pressure drop of the check valve in the forward direction is less than 1 psi. The break pressure in the reverse direction is greater than 100 psi. It should be understood, however, that modification of one or more components would alter the operating parameters of these valves. If the forward flow pressure is increased, there is, generally, a reduction in oxygen enriched gas production. If the break pressure for reverse flow is reduced or set too low, there is, generally, a reduction in oxygen enriched gas pressure.

In an example embodiment, canister 302 is pressurized by compressed air produced in compression system 200 and passed into canister 302. During pressurization of canister 302 inlet valve 122 is open, outlet valve 132 is closed, inlet valve 124 is closed and outlet valve 134 is open. Outlet valve 134 is opened when outlet valve 132 is closed to allow substantially simultaneous venting of canister 304 while canister 302 is pressurized. Canister 302 is pressurized until the pressure in canister is sufficient to open check valve 142. Oxygen enriched gas produced in canister 302 exits through check valve and, in one embodiment, is collected in accumulator 109 that serves as a storage container. Optionally, oxygen enriched gas outlet from the accumulator 109 through a conduit to the user may optionally be controlled by an additional valve (not shown in FIG. 1). Such a valve may also be operated by the controller 400 (such as with control of program instructions) and its operations may be responsive to a sensor signal such as from one or more signals from a sensor (not shown) such as a pressure or flow rate sensor.

After some period of time during pressurization, the gas separation adsorbent will become saturated with nitrogen and will be unable to separate additional significant amounts of nitrogen from incoming air. This point is usually reached after a predetermined time of oxygen enriched gas production during a production cycle. In the embodiment described above, when the gas separation adsorbent in canister 302 reaches this saturation point, the inflow of compressed air is stopped (by inlet valve 122) and canister 302 is vented (by outlet valve 132) to remove nitrogen. During venting, inlet valve 122 is closed, and outlet valve 132 is opened. While canister 302 is being vented, canister 304 is pressurized to produce oxygen enriched gas in the same manner described above. Pressurization of canister 304 is achieved by closing outlet valve 134 and opening inlet valve 124. The oxygen enriched gas exits canister 304 through check valve 144.

During venting of canister 302, outlet valve 132 is opened allowing pressurized gas (mainly nitrogen) to exit the canister through concentrator outlet 130. In an embodiment, the vented gases may be directed through outlet muffler 133 to reduce the noise produced by releasing the pressurized gas from the canister. As gas is released from canister 302, the pressure in the canister drops, allowing the nitrogen to become desorbed from the gas separation adsorbent. The released nitrogen exits the canister through outlet 130, resetting the canister to a state that allows renewed separation of oxygen from an air stream. Outlet muffler 133 may include open cell foam (or another material) to muffle the sound of the gas leaving the oxygen concentrator. In some embodiments, the combined muffling components/techniques for the input of air and the output of gas, may provide for oxygen concentrator operation at a sound level below 50 decibels.

During venting of the canisters, it is advantageous that at least a majority of the nitrogen is removed. In an embodiment, at least about 50%, at least about 60%, at least about 70%, at least about 80%, at least about 90%, at least about 95%, at least about 98%, or substantially all of the nitrogen in a canister is removed before the canister is re-used in another cycle to separate oxygen from air. In some embodiments, a canister may be further purged of nitrogen using an oxygen enriched stream that is introduced into the canister from the other canister.

In an example of such a purging process, a portion of the oxygen enriched gas may be transferred from canister 302 to canister 304 when canister 304 is being vented of nitrogen. Transfer of oxygen enriched gas from canister 302 to 304, during venting of canister 304, helps to further purge nitrogen (and other gases) from the canister. In an embodiment, oxygen enriched gas may travel through flow restrictors 151, 153, and 155 between the two canisters. Flow restrictor 151 may be a trickle flow restrictor. Flow restrictor 151, for example, may be a 0.009D flow restrictor (e.g., the flow restrictor has a radius 0.009" which is less than the diameter of the conduit or tube it is inside). Flow restrictors 153 and 155 may be 0.013D flow restrictors. Other flow restrictor types and sizes are also contemplated and may be used depending on the specific configuration and tubing or flow path used to couple the canisters. In some embodiments, the flow restrictors may be press fit flow restrictors that restrict air flow by introducing a narrower diameter in their respective tube or flow path. In some embodiments, the press fit flow restrictors may be made of sapphire, metal or plastic (other materials are also contemplated).

Flow of oxygen enriched gas is also controlled by use of valve 152 and valve 154. Thus, the controller 400 may also include program instructions for controlling a generation of valve control signals that control operations of the valves 152 and 154. For example, valves 152 and 154 may be opened for a short duration during the venting process (and may be closed otherwise) to prevent excessive oxygen loss out of the purging canister. Other durations are also contemplated. In an example, canister 302 is being vented and it is desirable to purge canister 302 by passing a portion of the oxygen enriched gas being produced in canister 304 into canister 302. A portion of oxygen enriched gas, upon pressurization of canister 304, will pass through flow restrictor 151 into canister 302 during venting of canister 302. Additional oxygen enriched gas is passed into canister 302, from canister 304, through valve 154 and flow restrictor 155. Valve 152 may remain closed during the transfer process, or may be opened if additional oxygen enriched gas is needed. The selection of appropriate flow restrictors 151 and 155, coupled with controlled opening of valve 154 allows a controlled amount of oxygen enriched gas to be sent from canister 304 to 302. In an embodiment, the controlled amount of oxygen enriched gas is an amount sufficient to purge canister 302 and minimize the loss of oxygen enriched gas through venting valve 132 of canister 302. While this embodiment describes venting of canister 302, it should be understood that the same process can be used to vent canister 304 using flow restrictor 151, valve 152 and flow restrictor 153.

The pair of equalization/vent valves 152/154 work with flow restrictors 153 and 155 to optimize the air flow balance between the two canisters. This may allow for better flow control for venting the canisters with oxygen enriched gas from the other of the canisters. It may also provide better flow direction between the two canisters. It has been found that, while flow valves 152/154 may be operated as bi-directional valves, the flow rate through such valves varies depending on the direction of fluid flowing through the valve. For example, oxygen enriched gas flowing from canister 304 toward canister 302 has a flow rate faster through valve 152 than the flow rate of oxygen enriched gas flowing from canister 302 toward canister 304 through valve 152. If a single valve was to be used, eventually either too much or too little oxygen enriched gas would be sent between the canisters and the canisters would, over time, begin to produce different amounts of oxygen enriched gas. Use of opposing valves and flow restrictors on parallel air pathways may equalize the flow pattern of the oxygen between the two canisters. Equalising the flow may allow for a steady amount of oxygen available to the user over multiple cycles and also may allow a predictable volume of oxygen to purge the other of the canisters. In some embodiments, the air pathway may not have restrictors but may instead have a valve with a built-in resistance or the air pathway itself may have a narrow radius to provide resistance.

At times, oxygen concentrator may be shut down for a period of time. When an oxygen concentrator is shut down, the temperature inside the canisters may drop as a result of the loss of adiabatic heat from the compression system. As the temperature drops, the volume occupied by the gases inside the canisters will drop. Cooling of the canisters may lead to a negative pressure in the canisters. Valves (e.g., valves 122, 124, 132, and 134) leading to and from the canisters are dynamically sealed rather than hermetically sealed. Thus, outside air may enter the canisters after shutdown to accommodate the pressure differential. When outside air enters the canisters, moisture from the outside air may condense inside the canister as the air cools. Condensation of water inside the canisters may lead to gradual degradation of the gas separation adsorbents, steadily reducing ability of the gas separation adsorbents to produce oxygen enriched gas.

In an example, outside air may be inhibited from entering canisters after the oxygen concentrator is shut down by pressurising both canisters prior to shutdown. For example, the controller 400 may control such an operation in a shutdown process or shutdown sequence by operating the compressor and controlling the valve(s) accordingly to create the pressurized condition. By storing the canisters under a positive pressure, the valves may be forced into a hermetically closed position by the internal pressure of the air in the canisters. In an embodiment, the pressure in the canisters, at shutdown, should be at least greater than ambient pressure. As used herein the term "ambient pressure" refers to the pressure of the surroundings in which the oxygen concentrator is located (e.g. the pressure inside a room, outside, in a plane, etc.). In an embodiment, the pressure in the canisters, at shutdown, is at least greater than standard atmospheric pressure (i.e., greater than 760 mmHg (Torr), 1 atm, 101,325 Pa). In an embodiment, the pressure in the canisters, at shutdown, is at least about 1.1 times greater than ambient pressure; is at least about 1.5 times greater than ambient pressure; or is at least about 2 times greater than ambient pressure.

In an embodiment, pressurization of the canisters may be achieved by directing pressurized air into each canister from the compression system and closing valves, or the pertinent canister related valves, to trap the pressurized air in the canisters. In an example, when a shutdown sequence is initiated, inlet valves 122 and 124 are opened and outlet valves 132 and 134 are closed. Because inlet valves 122 and 124 are joined together by a common conduit, both canisters 302 and 304 may become pressurized as air and or oxygen enriched gas from one canister may be transferred to the other canister. This situation may occur when the pathway between the compression system and the two inlet valves allows such transfer. Because the oxygen concentrator operates in an alternating pressurize/venting mode, at least one of the canisters should be in a pressurized state at any given time. In an alternate embodiment, the pressure may be increased in each canister by operation of compression system 200. When inlet valves 122 and 124 are opened, pressure between canisters 302 and 304 will equalize, however, the equalized pressure in either canister may not be sufficient to inhibit air from entering the canisters during shutdown. In order to ensure that air is inhibited from entering the canisters, compression system 200 may be operated for a time sufficient to increase the pressure inside both canisters to a level at least greater than ambient pressure. Regardless of the method of pressurization of the canisters, once the canisters are pressurized, inlet valves 122 and 124 are closed, trapping the pressurized air inside the canisters, which inhibits air from entering the canisters during the shutdown period. Achieving such a pressurized condition of the canisters may conclude the shutdown sequence. Such a pressure condition may optionally be detected such as by using an optional pressure sensor(s) in fluid communication with the canisters or conduits related thereto. Optionally, such a condition may be estimated by a timed operation of the compression system for a predetermined time given known characteristics of the compression system and canisters.

Figure 2:
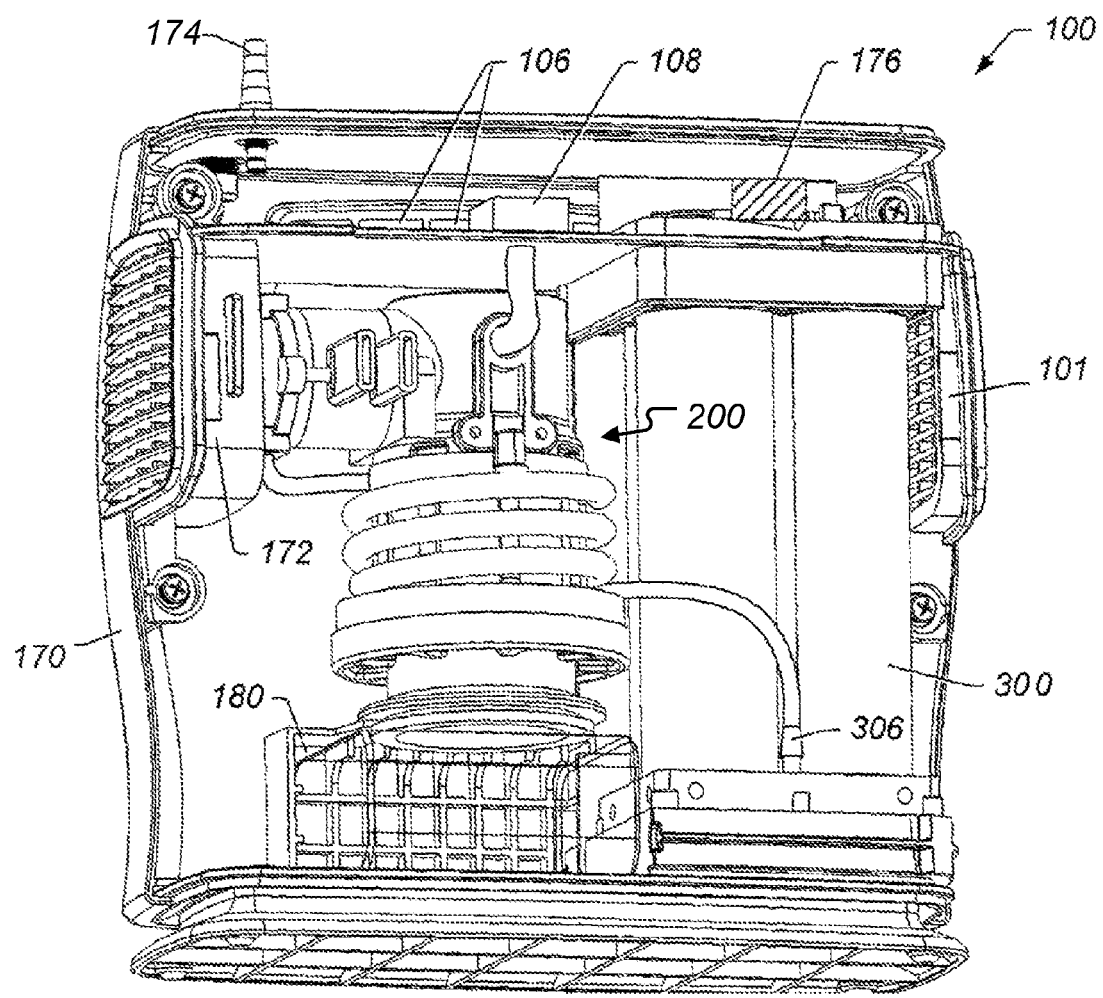
FIG. 2 depicts a side view of the main components of an example oxygen concentrator.

Referring to FIG. 2, an example oxygen concentrator 100 is depicted. Oxygen concentrator 100 includes a compression system 200, a canister assembly 300, and a power supply 180 disposed within an outer housing 170. Inlets 101 are located in outer housing 170 to allow air from the environment to enter oxygen concentrator 100. Inlets 101 may allow air to flow into the compartment to assist with cooling of the components in the compartment. Power supply 180 provides a source of power for the oxygen concentrator 100. Compression system 200 draws air in through the inlet 106 and inlet muffler 108. Inlet muffler 108 may reduce noise of air being drawn in by the compression system and also may include a desiccant material to remove water from the incoming air. Oxygen concentrator 100 may further include a fan such as near the outlet 172 used to vent air and other gases from the oxygen concentrator. An outlet port 174 fluidly coupled to the accumulator may provide a connection (e.g., interference fit type connector) for coupling to a conduit or tube for gas delivery such as for a nasal cannula.

Compression System

Figure 3A:
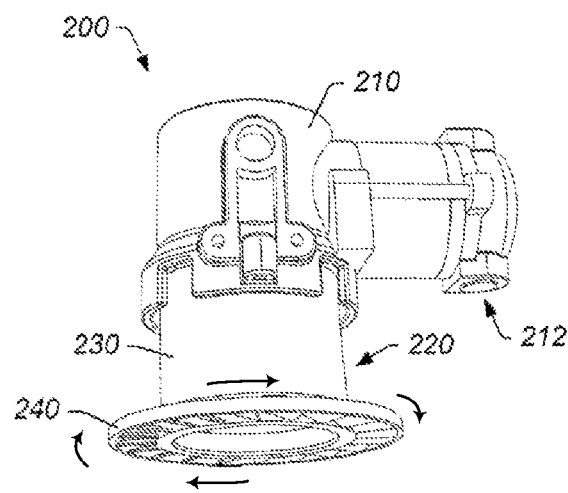
FIG. 3A depicts a perspective side view of an example compression system.
Figure 3B:
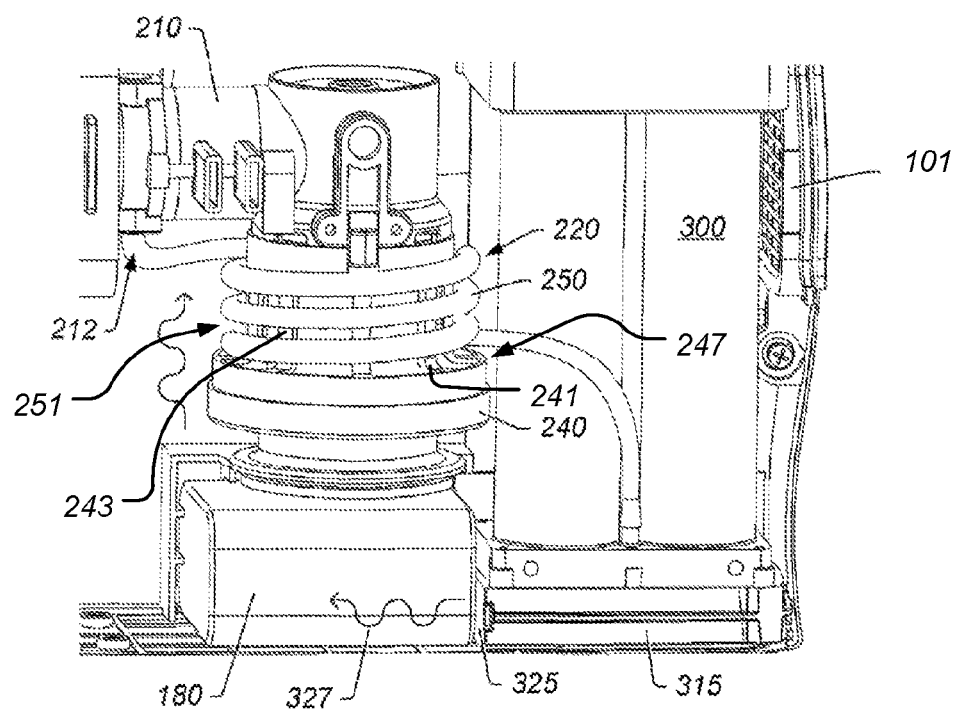
FIG. 3B depicts a side view of an example compression system that includes a heat exchange conduit.

In some embodiments, compression system 200 includes one or more compressors. In another embodiment, compression system 200 includes a single compressor, coupled to all of the canisters of canister system 300. Turning to FIGS. 3A and 3B, an example compression system 200 is depicted that includes compressor 210 and motor 220. Motor 220 is coupled to compressor 210 and provides an operating force to the compressor to operate the compression mechanism. For example, motor 220 may be a motor providing a rotating component (e.g., an eccentric bearing) that causes cyclical motion of a component (e.g., a piston) of the compressor that compresses air. When compressor 210 is a piston type compressor, motor 220 provides an operating force which causes the piston of compressor 210 to be reciprocated. Reciprocation of the piston causes compressed air to be produced by compressor 210. The pressure of the compressed air is, in part, estimated by the speed at which the compressor is operated (e.g., how fast the piston is reciprocated). Motor 220, therefore, may be a variable speed motor that is operable at various speeds to dynamically control the pressure of air produced by compressor 210.

In one embodiment, compressor 210 includes a single head wobble type compressor having a piston. Other types of compressors may be used such as diaphragm compressors and other types of piston compressors. Motor 220 may be a DC or AC motor and provides the operating power to the compressing component of compressor 210. Motor 220, in an embodiment, may be a brushless DC motor. Motor 220 may be a variable speed motor capable of operating the compressing component of compressor 210 at variable speeds. Motor 220 may be coupled to controller 400, as depicted in FIG. 1, which sends operating signals to the motor to control the operation of the motor. For example, controller 400, such as in accordance with program instructions of one or more processors of the controller, may send signals to motor 220 to: turn the motor on, turn motor the off, and set the operating speed of motor.

Compression system 200 inherently creates substantial heat. Heat is caused by the consumption of power by motor 220 and the conversion of power into mechanical motion. Compressor 210 generates heat due to the increased resistance to movement of the compressor components by the air being compressed. Heat is also inherently generated due to adiabatic compression of the air by compressor 210. Thus, the continual pressurization of air produces heat in the enclosure (e.g., housing 170). Additionally, power supply 180 may produce heat as power is supplied to compression system 200. Furthermore, users of the oxygen concentrator may operate the device in unconditioned environments (e.g., outdoors) at potentially higher ambient temperatures than indoors, thus the incoming air will already be in a heated state.

Heat produced inside oxygen concentrator 100 can be problematic. Lithium ion batteries are generally employed as a power source for oxygen concentrators due to their long life and light weight. Lithium ion battery packs, however, are dangerous at elevated temperatures and safety controls are employed in oxygen concentrator 100 to shut down the system if dangerously high power supply temperatures are detected. Additionally, as the internal temperature of oxygen concentrator 100 increases, the amount of oxygen generated by the concentrator may decrease. This is due, in part, to the decreasing amount of oxygen in a given volume of air at higher temperatures. If the amount of produced oxygen drops below a predetermined amount, the oxygen concentrator 100 may automatically shut down, such as when a sensor detects the low level of oxygen concentration in the produced gas.

Because of the compact nature of oxygen concentrators, dissipation of heat can be difficult. Solutions typically involve the use of one or more fans to create a flow of cooling air through the enclosure. Such solutions, however, require additional power from the power supply and thus shorten the portable usage time of the oxygen concentrator. In an embodiment, a passive cooling system may be used that takes advantage of the mechanical power produced by motor 220. Referring to FIGS. 3A and 3B, compression system 200 includes motor 220 having an external rotating armature 230. Specifically, armature 230 of motor 220 (e.g. a DC motor) is wrapped around the stationary field that is driving the armature. Since motor 220 is a large contributor of heat to the overall system it is helpful to pull heat off of the motor and sweep it out of the enclosure. With the external high-speed rotation, the relative velocity of the major component of the motor and the air in which it exists is very high. The surface area of the armature is larger if externally mounted than if it is internally mounted. Since the rate of heat exchange is proportional to the surface area and the square of the velocity, using a larger surface area armature mounted externally increases the ability of heat to be dissipated from motor 220. The gain in cooling efficiency by mounting the armature externally, allows the elimination of one or more cooling fans that are discrete from the compression system motor, thus reducing the weight and power consumption while maintaining the interior of the oxygen concentrator within the appropriate temperature range. Thus, additional motor(s) might not be required such as for an addition fan. Additionally, the rotation of the externally mounted armature creates movement of air proximate to the motor to promote additional cooling.

Moreover, an external rotating armature may help the efficiency of the motor, allowing less heat to be generated. A motor having an external armature operates similar to the way a flywheel works in an internal combustion engine. When the motor is driving the compressor, the resistance to rotation is low at low pressures. When the pressure of the compressed air is higher, the resistance to rotation of the motor is higher. As a result, the motor does not maintain consistent ideal rotational stability, but instead surges and slows down depending on the pressure demands of the compressor. This tendency of the motor to surge and then slow down is inefficient and therefore generates heat. Use of an external armature adds greater angular momentum to the motor which helps to compensate for the variable resistance experienced by the motor. Since the motor does not have to work as hard, the heat produced by the motor may be reduced.

In an embodiment, cooling efficiency may be further increased by coupling an air transfer device 240 to external rotating armature 230. In an embodiment, air transfer device 240 is coupled to the external armature 230 such that rotation of the external armature causes the air transfer device to create an airflow that passes over at least a portion of the motor. In an embodiment, air transfer device includes one or more fan blades 241, 243 coupled to the armature. In an embodiment, a plurality of fan blades may be arranged in an annular ring such that the air transfer device acts as an impeller 247 that is rotated by movement of the external rotating armature. As depicted in FIGS. 3A and 3B, air transfer device 240 may be mounted to an outer surface of the external armature 230, in alignment with the motor. The mounting of the air transfer device to the armature allows airflow to be directed toward the main portion of the external rotating armature, providing a cooling effect during use. In an embodiment, the air transfer device directs air flow such that a majority of the external rotating armature is in the air flow path.

Further, referring to FIGS. 3A and 3B, air pressurized by compressor 210 exits compressor 210 at compressor outlet 212. A compressor outlet conduit 250 is coupled to compressor outlet 212 to transfer the compressed air to canister system 300. As noted previously, compression of air causes an increase in the temperature of the air. This increase in temperature can be detrimental to the efficiency of the oxygen concentrator. In order to reduce the temperature of the pressurized air, compressor outlet conduit 250 is placed in the air flow path produced by air transfer device 240. At least a portion of compressor outlet conduit 250 may be positioned proximate to motor 220. Thus, airflow, created by air transfer device, may contact both motor 220 and compressor outlet conduit 250. In one embodiment, a majority of compressor outlet conduit 250 is positioned proximate to motor 220. In an embodiment, the compressor outlet conduit 250 is coiled around motor 220, as depicted in FIG. 3B. For example, the outlet conduit may spiral about the blades of an impeller of the air transfer device. Gaps 251 may optionally be implemented between the coils of the spiral to promote air movement between coils of the conduit 250 for improving the cooling efficiency.

In an embodiment, the compressor outlet conduit 250 is composed of a heat exchange metal. Heat exchange metals include, but are not limited to, aluminum, carbon steel, stainless steel, titanium, copper, copper-nickel alloys or other alloys formed from combinations of these metals. Thus, compressor outlet conduit 250 can act as a heat exchanger to remove heat that is inherently caused by compression of the air. By removing heat from the compressed air, the number of molecules in a given volume at a given pressure is increased. As a result, the amount of oxygen that can be generated by each canister during each pressure swing cycle may be increased.

The heat dissipation mechanisms described herein are either passive or make use of elements required for the oxygen concentrator 100. Thus, for example, dissipation of heat may be increased without using systems that require additional power. By not requiring additional power, the run-time of the battery packs may be increased and the size and weight of the oxygen concentrator may be minimized. Likewise, use of an additional box fan or cooling unit may be eliminated. Eliminating such additional features reduces the weight and power consumption of the oxygen concentrator.

As discussed above, adiabatic compression of air causes the air temperature to increase. During venting of a canister in canister system 300, the pressure of the gas being released from the canisters decreases. The adiabatic decompression of the gas in the canister causes the temperature of the gas to drop as it is vented. Thus, in some versions of the oxygen concentrator, the cooled vented gases from canister system 300 may be directed toward power supply 180 and/or toward compression system 200 to utilize the temperature drop. In an example, base 315 of canister system 300 receives the vented gases from the canisters. The vented gases 327 (e.g., nitrogen enriched, oxygen depleted air) are directed through one or more flow paths of the base 315 toward outlet 325 of the base and toward power supply 180. The vented gases, as noted, are cooled due to decompression of the gases and therefore passively provide cooling to the power supply. When the compression system is operated, the air transfer device will gather the cooled vented gases and direct the gases toward the motor of compression system 200. Optional fan near outlet 172 may also assist in directing the vented gas across compression system 200 and out of the housing 170. In this manner, additional cooling may be obtained without requiring any further power requirements from the battery.

Outlet System

An outlet system, coupled to one or more of the canisters, includes one or more conduits for providing oxygen enriched gas to a user. In an embodiment, oxygen enriched gas produced in either of canisters 302 and 304 is collected in accumulator 109 through check valves 142 and 144, respectively, as depicted schematically in FIG. 1. The oxygen enriched gas leaving the canisters may be collected in an oxygen accumulator 109 prior to being provided to a user. In some embodiments, a tube may be coupled to the accumulator 109, such as via the outlet port 174, to provide the oxygen enriched gas to the user. Oxygen enriched gas may be delivered to the user through an airway delivery device (e.g., conduit and cannula) that transfers the oxygen enriched gas to the user's mouth and/or nose. In an embodiment, an outlet may include a tube that directs the oxygen toward a user's nose and/or mouth that may not be directly coupled to the user's nose.

Figure 4A:
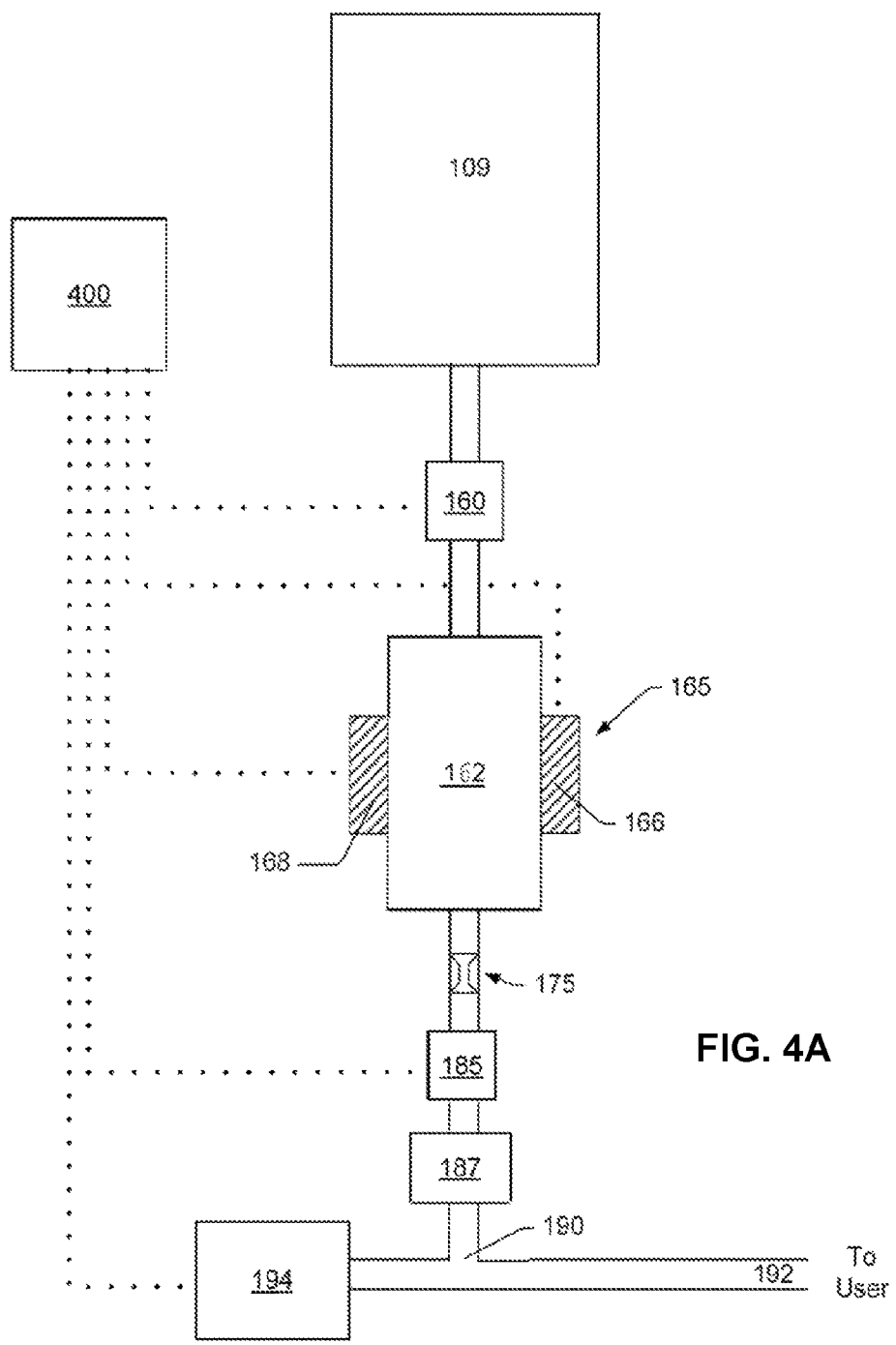
FIG. 4A is a schematic diagram of the outlet components of an oxygen concentrator.

Turning to FIG. 4A, a schematic diagram of an embodiment of an outlet system for an oxygen concentrator is shown. A supply valve 160 may be coupled to outlet tube to control the release of the oxygen enriched gas from accumulator 109 to the user. In an embodiment, supply valve 160 is an electromagnetically actuated plunger valve. Supply valve 160 is actuated by controller 400, by generating supply valve control signals that may be set according to control of the program instructions of the controller 400, to control the delivery of oxygen enriched gas to a user. Actuation of supply valve 160 typically is not timed or synchronized to the pressure swing adsorption process. Instead, actuation may be synchronized to the user's breathing. Additionally, supply valve 160 may have continuously-valued or quantified actuation to enable provision of oxygen enriched gas according to a predetermined amplitude profile as discussed in more detail herein. A proportional valve is an example of such a continuously-actuatable supply valve 160 that may be implemented.

Oxygen enriched gas in accumulator 109 passes through supply valve 160 into expansion chamber 162 as depicted in FIG. 4A. In an embodiment, expansion chamber 162 may include one or more devices that may be implemented to determine an oxygen concentration of gas passing through the chamber. Oxygen enriched gas in expansion chamber 162 builds briefly, through release of gas from accumulator 109 by supply valve 160, and then may be bled through a small orifice flow restrictor 175 to a flow rate sensor 185 and then to particulate filter 187. Flow restrictor 175 may be a 0.025 D flow restrictor. Other flow restrictor types and sizes may be used. In some embodiments, the diameter of the air pathway in the housing may be restricted to create restricted air flow. Flow rate sensor 185 may be any sensor capable of generating or inferring a signal representative of the rate of oxygen enriched gas flowing through the conduit. Particulate filter 187 may be used to filter bacteria, dust, granule particles, etc. prior to delivery of the oxygen enriched gas to the user. The oxygen enriched gas passes through filter 187 to connector 190 which sends the oxygen enriched gas to the user via conduit 192 and to pressure sensor 194. In some embodiments, pressure sensor 194 may generate a signal that is proportional to the amount of positive or negative pressure applied to a sensing surface.

The controller 400, in accordance with its program instructions implemented with the methodologies described in more detail herein, may receive the flow rate signal from the flow rate sensor 185 as a feedback signal to enable a closed-loop control of a continuously-valued actuation of the supply valve 160. Such continuously-valued actuation of the supply valve 160 may control gas release in order to deliver a bolus of oxygen enriched gas according to a predetermined amplitude profile. Such controlled, continuously-valued actuation of supply valve 160 may result in a bolus of oxygen being provided at the correct time and according to an amplitude profile that assures rapid delivery into the user's lungs with minimal retrograde flow waste and/or anatomic deadspace waste. When the bolus can be delivered in this manner, there may be a linear relationship between a prescribed continuous flow rate and a therapeutically equivalent bolus volume in pulsed delivery mode for a user at rest with a given breathing pattern. For example, the total volume of each bolus required to emulate a continuous-flow prescription may be equal to 11 mL (per bolus) for each LPM of prescribed continuous flow rate, i.e., an 11 mL volume bolus for a prescription of 1 LPM; a 22 mL volume bolus for a prescription of 2 LPM; a 33 mL volume bolus for a prescription of 3 LPM; a 44 mL volume bolus for a prescription of 4 LPM; a 55 mL volume bolus for a prescription of 5 LPM; etc. This amount of the bolus volume (11 mL in this example) is referred to as the LPM equivalent bolus volume. It should be understood that the LPM equivalent bolus volume may vary between oxygen concentrators due to differences in construction design, tubing size, chamber size, etc. The LPM equivalent bolus volume will also vary depending on the user's breathing pattern.

Expansion chamber 162 may include one or more oxygen sensors that may be implemented for determining an oxygen concentration of gas passing through the chamber. In an embodiment, the oxygen concentration of gas passing through expansion chamber 162 is estimated using an oxygen sensor 165. An oxygen sensor is a device capable of detecting oxygen in a gas. Examples of oxygen sensors include, but are not limited to, ultrasonic oxygen sensors, electrical oxygen sensors, and optical oxygen sensors. In one embodiment, oxygen sensor 165 is an ultrasonic oxygen sensor that includes an ultrasonic emitter 166 and an ultrasonic receiver 168. In some embodiments, ultrasonic emitter 166 may include multiple ultrasonic emitters and ultrasonic receiver 168 may include multiple ultrasonic receivers. In embodiments having multiple emitters/receivers, the multiple ultrasonic emitters and multiple ultrasonic receivers may be axially aligned (e.g., across the gas mixture flow path which may be perpendicular to the axial alignment).

The ultrasonic oxygen sensor in use, directs an ultrasonic sound wave (from emitter 166) through oxygen enriched gas disposed in chamber 162 to receiver 168. Ultrasonic sensor assembly may be based on detecting the speed of sound through the gas mixture to determine the composition of the gas mixture (e.g., the speed of sound is different in nitrogen and oxygen). In a mixture of the two gases, the speed of sound through the mixture may be an intermediate value proportional to the relative amounts of each gas in the mixture. In use, the sound at the receiver 168 is slightly out of phase with the sound sent from emitter 166. This phase shift is due to the relatively slow velocity of sound through a gas medium as compared with the relatively fast speed of the electronic pulse through wire. The phase shift, then, is proportional to the distance between the emitter and the receiver and the speed of sound through the expansion chamber. The density of the gas in the chamber affects the speed of sound through the chamber and the density is proportional to the ratio of oxygen to nitrogen in the chamber. Therefore, the phase shift can be used to measure the concentration of oxygen in the expansion chamber. In this manner the relative concentration of oxygen in the accumulator 109 may be estimated as a function of one or more properties of a detected sound wave traveling through expansion chamber 162.

In some embodiments, multiple emitters 166 and receivers 168 may be used. The readings from the emitters 166 and receivers 168 may be averaged to cancel errors that may be inherent in turbulent flow systems. In some embodiments, the presence of other gases may also be detected by measuring the transit time and comparing the measured transit time to predetermined transit times for other gases and/or mixtures of gases.

The sensitivity of the ultrasonic sensor system may be increased by increasing the distance between the emitter 166 and receiver 168, for example to allow several sound wave cycles to occur between emitter 166 and the receiver 168. In some embodiments, if at least two sound cycles are present, the influence of structural changes of the transducer may be reduced by measuring the phase shift relative to a fixed reference at two points in time. If the earlier phase shift is subtracted from the later phase shift, the shift caused by thermal expansion of expansion chamber 162 may be reduced or cancelled. The shift caused by a change of the distance between the emitter 166 and receiver 168 may be approximately the same at the measuring intervals, whereas a change owing to a change in oxygen concentration may be cumulative. In some embodiments, the shift measured at a later time may be multiplied by the number of intervening cycles and compared to the shift between two adjacent cycles. Further details regarding sensing of oxygen in the expansion chamber may be found, for example, in U.S. Published Patent Application No. 2009-0065007, published Mar. 12, 2009, and entitled "Oxygen Concentrator Apparatus and Method, which is incorporated herein by reference.

Flow rate sensor 185 may be used to determine the flow rate of oxygen enriched gas flowing through the outlet system. Flow rate sensors that may be used include, but are not limited to: diaphragm/bellows flow meters; rotary flow meters (e.g. Hall effect flow meters); turbine flow meters; orifice flow meters; and ultrasonic flow meters. Flow rate sensor 185 may be coupled to controller 400 to provide a flow rate signal to the controller 400. The flow rate of gas flowing through the outlet system may be an indication of the relative breathing volume of the user. Changes in the flow rate of gas flowing through the outlet system may also be used to determine a breathing rate of the user. Controller 400 may control actuation of supply valve 160 based on the breathing rate and/or breathing volume of the user, as estimated by flow rate sensor 185 by evaluation/processing of the flow rate signal at the controller 400.

In some embodiments, ultrasonic sensor system 165 and, for example, flow rate sensor 185 may provide a measurement of an actual amount of oxygen being provided. For example, flow rate sensor 185 may provide a signal to the controller 400 for the controller to determine a volume of gas (based on the flow rate signal) provided and ultrasonic sensor system 165 may provide a signal to the controller 400 for the controller 400 to determine the concentration of oxygen of the volume of gas provided. These two measurements together may be used by controller 400 to determine an approximation of the actual amount of oxygen provided to the user.

As previously mentioned, oxygen enriched gas passes through flow rate sensor 185 to filter 187. Filter 187 removes bacteria, dust, granule particles, etc. prior to providing the oxygen enriched gas to the user. The filtered oxygen enriched gas passes through filter 187 to optional connector 190. Connector 190 may be a "Y" connector coupling the outlet of filter 187 to pressure sensor 194 and outlet conduit 192. Pressure sensor 194 may be implemented with the controller 400 to monitor the pressure of the gas passing through conduit 192 to the user. Changes in pressure sensed by pressure sensor 194 may be evaluated by the controller 400 to determine a breathing rate of a user, as well as the onset of inhalation (also referred to as the trigger instant). Controller 400 may control actuation of supply valve 160 based on the breathing rate and/or onset of inhalation of the user, as estimated using pressure sensor 194 as described below. In an embodiment, controller 400 may control actuation of supply valve 160 based on information provided by flow rate sensor 185 and pressure sensor 194.

Figure 4B:
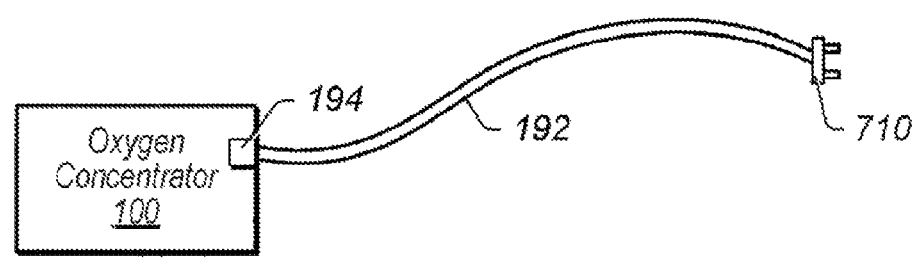
FIG. 4B depicts an outlet conduit for an oxygen concentrator.
Figure 4C:
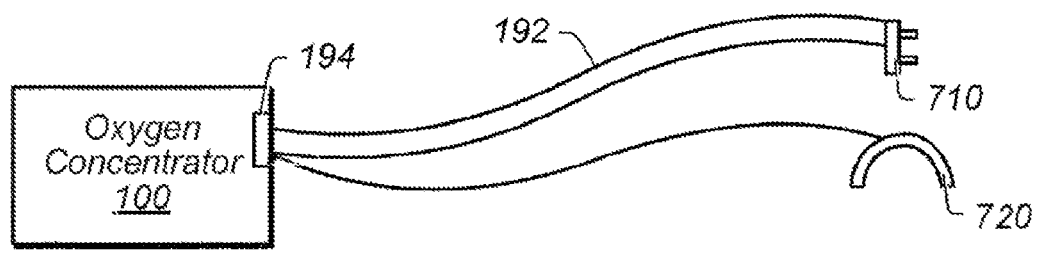
FIG. 4C depicts an alternate outlet conduit for an oxygen concentrator.

Oxygen enriched gas may be provided to a user through conduit 192, that may be coupled to the optional outlet port 174. In an embodiment, conduit 192 may be a silicone tube. Conduit 192 may be coupled to a user using an airway delivery device 710, as depicted in FIGS. 4B and 4C. Airway delivery device 710 may be any device capable of providing the oxygen enriched gas to nasal cavities. Examples of airway delivery devices include, but are not limited to: nasal masks, nasal pillows, nasal prongs, and nasal cannulas. A nasal cannula airway delivery device is depicted in FIG. 4B. During use, oxygen enriched gas from oxygen concentrator 100 is provided to the user through conduit 192 and airway coupling member 710. Airway delivery device 710 is positioned proximate to a user's airway (e.g., proximate to the user's mouth and or nose) to allow delivery of the oxygen enriched gas to the user while allowing the user to breathe air from the surroundings.

During use, oxygen enriched gas may be directed/released to airway delivery device 710 when a change in pressure is sensed proximate to the airway delivery device 710 by controller 400 detecting the pressure change and controlling activating supply valve 160. In one embodiment, airway delivery device 710 may be coupled to a pressure sensor. When a user inhales air through their nose, the pressure sensor may detect the onset of inhalation as a drop in pressure proximate to the airway delivery device 710. Controller 400 of oxygen concentrator 100 may provide a bolus of oxygen enriched gas to the user at the onset of inhalation.

In an alternate embodiment, a mouthpiece may be used to provide oxygen enriched gas to the user. As shown in FIG. 4C, a mouthpiece 720 may be coupled to oxygen concentrator 100. Mouthpiece 720 may be the only device used to provide oxygen enriched gas to the user, or a mouthpiece may be used in combination with a nasal airway delivery device (e.g., a nasal cannula). As depicted in FIG. 4C, oxygen enriched gas may be provided to a user through both a nasal airway delivery device 710 and a mouthpiece 720.

Mouthpiece 720 is removably positionable in a user's mouth. In one embodiment, mouthpiece 720 is removably couplable to one or more teeth in a user's mouth. During use, oxygen enriched gas is directed into the user's mouth via the mouthpiece. Mouthpiece 720 may be a night guard mouthpiece which is molded to conform to the user's teeth. Alternatively, mouthpiece may be a mandibular repositioning device. In an embodiment, at least a majority of the mouthpiece is positioned in a user's mouth during use.

During use, oxygen enriched gas may be directed to mouthpiece 720 when a change in pressure is detected proximate to the mouthpiece 720. In one embodiment, mouthpiece 720 may be coupled to a pressure sensor. When a user inhales air through their mouth, the pressure sensor may detect the onset of inhalation as a drop in pressure proximate to the mouthpiece 720. Controller 400 of oxygen concentrator 100 may provide a bolus of oxygen enriched gas to the user at the onset of inhalation.

During typical breathing of an individual, inhalation may occur through the nose, through the mouth or through both the nose and the mouth. Furthermore, breathing may change from one passageway to another depending on a variety of factors. For example, during more active activities, a user may switch from breathing through their nose to breathing through their mouth, or breathing through their mouth and nose. A system that relies on a single mode of delivery (either one of nasal and oral but not both), may not function properly if breathing through the monitored pathway is stopped. For example, if a nasal cannula is used to provide oxygen enriched gas to the user, an inhalation sensor (e.g., a pressure sensor or flow rate sensor) may be coupled to the nasal cannula to determine the onset of inhalation. If the user stops breathing through their nose, and switches to breathing through their mouth, the oxygen concentrator 100 may not know when to provide the oxygen enriched gas since there is no pressure drop detectable via the nasal cannula. Under such circumstances, oxygen concentrator 100 may increase the flow rate and/or increase the frequency of providing oxygen enriched gas until the inhalation sensor detects an inhalation by the user. If the user switches between breathing modes often, the default mode of providing oxygen enriched gas will cause the oxygen concentrator 100 to work harder, limiting the portable usage time of the system.

In an embodiment, a mouthpiece 720 is used in combination with an airway delivery device 710 (e.g., a nasal cannula) to provide oxygen enriched gas to a user, as depicted in FIG. 4C. Both mouthpiece 720 and airway delivery device 710 are coupled to an inhalation sensor. In one embodiment, mouthpiece 720 and airway delivery device 710 are coupled to the same inhalation sensor. In an alternate embodiment, mouthpiece 720 and airway delivery device 710 are coupled to different inhalation sensors. In either embodiment, the inhalation sensor(s) may detect the onset of inhalation from either the mouth or the nose. Oxygen concentrator 100 may be configured to provide oxygen enriched gas to the particular device (i.e. one of mouthpiece 720 and airway delivery device 710) proximate to which the onset of inhalation was detected. For example, the flow path from the accumulator may split/branch to each of the mouthpiece and airway delivery device and each branch may have a supply valve controlled by controller 400. Alternatively, an electromechanical three-way valve may be implemented as a supply valve and controlled by the controller 400 to selectively direct the bolus to the desired branch of the flow path (i.e., one of the mouthpiece 720 and airway delivery device 710). Alternatively, oxygen enriched gas may be provided to both mouthpiece 720 and the airway delivery device 710 if onset of inhalation is detected proximate either device. The use of a dual delivery system such as depicted in FIG. 4C may be particularly useful for users when they are sleeping and switch between nose breathing and mouth breathing without conscious effort.

Controller System

Operation of oxygen concentrator 100 may be performed automatically using an internal controller 400 coupled to various components of the oxygen concentrator 100, as described herein. Controller 400 includes one or more processors 410 and internal memory 420, as depicted in FIG. 1. Methodologies implemented to operate and monitor oxygen concentrator 100 as described in more detail herein may be implemented by program instructions stored in memory 420 or a carrier medium coupled to controller 400, and executed by one or more processors 410. A memory medium may include any of various types of memory devices or storage devices. The term "memory medium" is intended to include an installation medium, e.g., a Compact Disc Read Only Memory (CD-ROM), floppy disks, or tape device; a computer system memory or random access memory such as Dynamic Random Access Memory (DRAM), Double Data Rate Random Access Memory (DDR RAM), Static Random Access Memory (SRAM), Extended Data Out Random Access Memory (EDO RAM), Rambus Random Access Memory (RAM), etc.; or a non-volatile memory such as a magnetic media, e.g., a hard drive, or optical storage. The memory medium may comprise other types of memory as well, or combinations thereof. In addition, the memory medium may be located in a first computer in which the programs are executed, or may be located in a second different computer that connects to the first computer over a network, such as the Internet. In the latter instance, the second computer may provide program instructions to the first computer for execution. The term "memory medium" may include two or more memory mediums that may reside in different locations, e.g., in different computers that are connected over a network.

In some embodiments, controller 400 includes one or more processor(s) 410 that includes, for example, one or more field programmable gate arrays (FPGAs), microcontrollers, etc. included on a circuit board disposed in oxygen concentrator 100. Processor 410 is capable of executing program instructions stored in memory 420. In some embodiments, program instructions may be built into processor 410 such that a memory external to the processor may not be separately accessed (i.e., the memory 420 may be internal to the processor 410).

Processor 410 may be electronically coupled (e.g., wired or wirelessly) to various components of oxygen concentrator 100, including, but not limited to compression system 200, one or more of the valves used to control fluid flow through the system (e.g., valves 122, 124, 132, 134, 152, 154, 160), oxygen sensor 165, pressure sensor 194, flow rate sensor 185, temperature sensors, fans, and any other component that may be electrically controlled. In some embodiments, a separate processor (and/or memory) may be coupled to one or more of the components.

Controller 400 is programmed with program instructions as described herein to operate oxygen concentrator 100 and is further programmed to monitor the oxygen concentrator 100 for malfunction states. For example, in one embodiment, controller 400 is programmed to trigger an alarm if the system is operating and no breathing is detected by the user for a predetermined amount of time. For example, if controller 400 does not detect a breath for a period of 75 seconds, an alarm LED may be lit and/or an audible alarm may be sounded. If the user has truly stopped breathing, for example, during a sleep apnea episode, the alarm may be sufficient to awaken the user, causing the user to resume breathing. The action of breathing may be sufficient for controller 400 to reset this alarm function. Alternatively, if the system is accidently left on when output conduit 192 is removed from the user, the alarm may serve as a reminder for the user to turn oxygen concentrator 100 off.

Controller 400 is further coupled to oxygen sensor 165, and may be programmed for continuous or periodic monitoring of the oxygen concentration of the oxygen enriched gas passing through expansion chamber 162. A minimum oxygen concentration threshold may be programmed into controller 400, such that the controller lights an LED visual alarm and/or an audible alarm to warn the user of the low concentration of oxygen.

Controller 400 is also coupled to internal power supply 180 and is configured to monitor the level of charge of the internal power supply. A minimum voltage and/or current threshold may be programmed into controller 400, such that the controller lights an LED visual alarm and/or an audible alarm to warn the user of low power condition. The alarms may be activated intermittently and at an increasing frequency as the battery approaches zero usable charge.

Further functions or methodologies of controller 400 are described in detail in other sections of this disclosure.

Outer Housing—Control Panel

Figure 5:
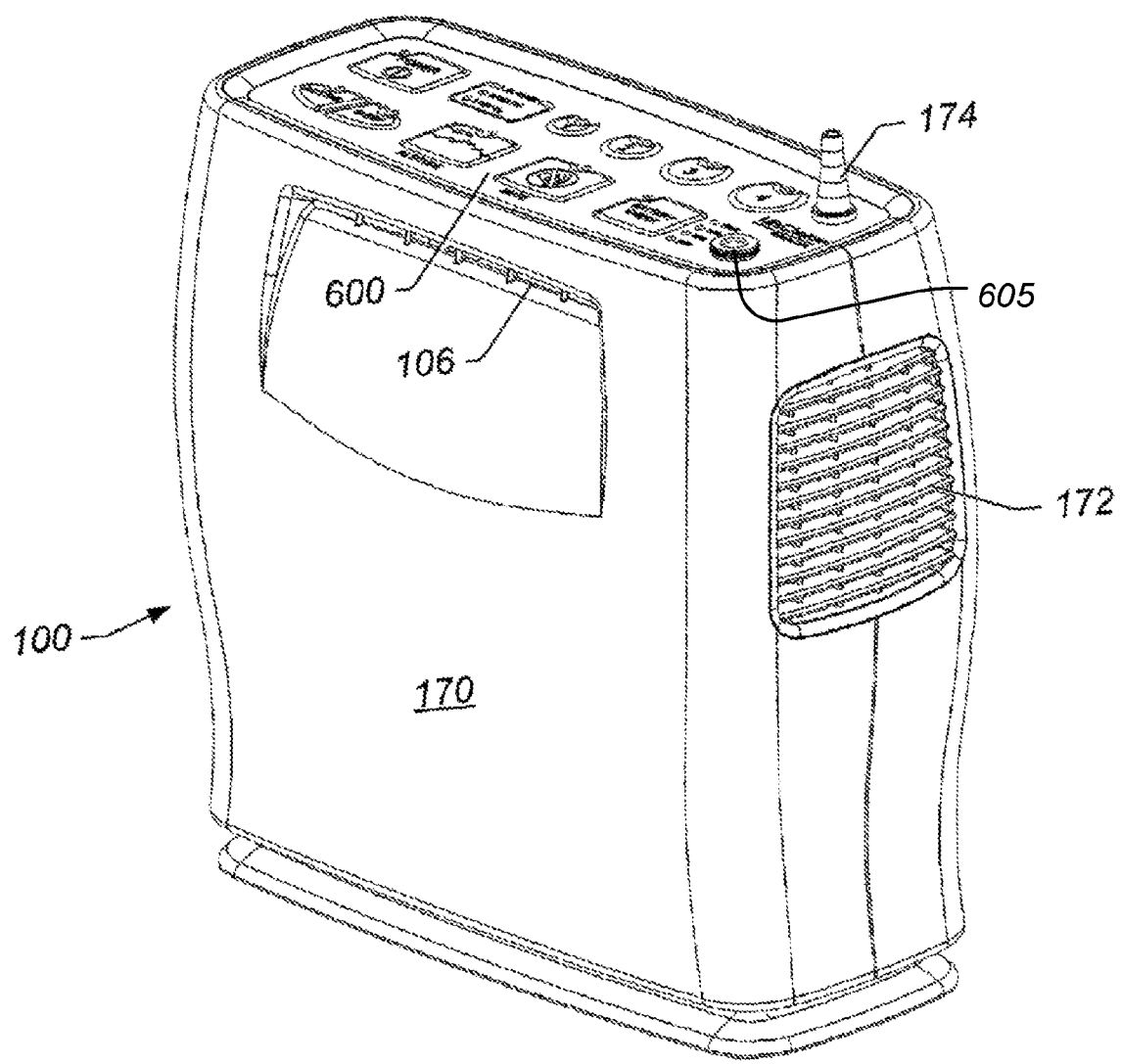
FIG. 5 depicts an outer housing for an example oxygen concentrator.

FIG. 5 depicts an embodiment of an outer housing 170 of an oxygen concentrator 100. In some embodiments, outer housing 170 may be comprised of a light-weight plastic. Outer housing includes compression system inlets 106, cooling system passive inlet 101 and outlet 172 at each end of outer housing 170, outlet port 174, and control panel 600. Inlet 101 and outlet 172 allow cooling air to enter the housing, flow through the housing, and exit the interior of housing 170 to aid in cooling of the oxygen concentrator 100. Compression system inlets 106 allow air to enter the compression system. Outlet port 174 is used to attach a conduit to provide oxygen enriched gas produced by the oxygen concentrator 100 to a user.

Figure 6:
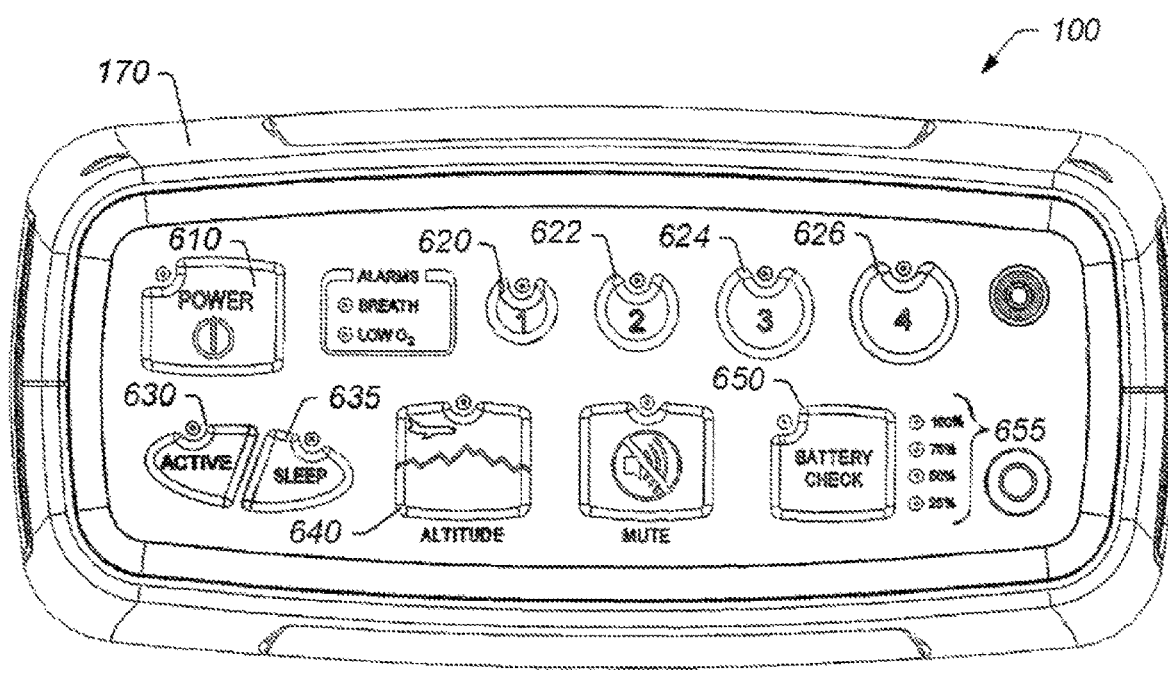
FIG. 6 depicts an example control panel for an oxygen concentrator.

Control panel 600 serves as an interface between a user and controller 400 to allow the user to initiate predetermined operation modes of the oxygen concentrator 100 and to monitor the status of the system. Charging input port 605 may be disposed in control panel 600. FIG. 6 depicts an example control panel 600.

In some embodiments, control panel 600 may include buttons to activate various operation modes for the oxygen concentrator 100. For example, control panel may include power button 610, dosage buttons 620, 622, 624, 626, active mode button 630, sleep mode button 635, and a battery check button 650. In some embodiments, one or more of the buttons may have a respective LED that may illuminate when the respective button is pressed (and may power off when the respective button is pressed again). Power button 610 may power the system on or off. If the power button is activated to turn the system off, controller 400 may initiate a shutdown sequence to place the system in a shutdown state (e.g., a state in which both canisters are pressurized as previously described). Dosage buttons 620, 622, 624, and 626 allow the prescribed continuous flow rate of oxygen enriched gas to be selected (e.g., 1 LPM by button 620, 2 LPM by button 622, 3 LPM by button 624, and 4 LPM by button 626). Such buttons may cause the oxygen concentrator 100 to deliver a rate of oxygen, when in a pulsed or demand mode, at an LPM equivalent bolus volume that corresponds to the continuous rate selected as described herein. Altitude button 640 may be selected when a user is going to be in a location at a higher elevation than the oxygen concentrator 100 is regularly used by the user.

Battery check button 650 initiates a battery check routine in the oxygen concentrator 100 which results in a relative battery power remaining LED 655 being illuminated on control panel 600.

A user may have a low breathing rate or depth if relatively inactive (e.g., asleep, sitting, etc.). The user may have a high breathing rate or depth if relatively active (e.g., walking, exercising, etc.). An active mode or an inactive mode may be activated automatically by comparing the detected breathing rate or depth to a threshold. Additionally, or alternatively, the user may manually activate a respective active or inactive mode by pressing button 630 for active mode and button 635 for inactive (sleep) mode. The adjustments made by the oxygen concentrator 100 in response to activating active mode or inactive mode are described in more detail herein.

Methods of Delivery of Oxygen Enriched Gas

The main use of an oxygen concentrator 100 is to provide supplemental oxygen to a user. Generally, the flow rate of supplemental oxygen to be provided is estimated and prescribed by a physician. Typical prescribed continuous flow rates of supplemental oxygen may range from about 1 LPM to up to about 10 LPM. The most commonly prescribed continuous flow rates are 1 LPM, 2 LPM, 3 LPM, and 4 LPM.

In order to minimize the amount of oxygen enriched gas that is needed to be produced while still emulating the effect of continuous flow at a prescribed continuous flow rate, controller 400 may be programmed to synchronise delivery of the oxygen enriched gas with the user's inhalations, a mode known as pulsed oxygen delivery (POD) or demand oxygen delivery. Releasing the oxygen enriched gas to the user only as the user inhales may prevent unnecessary oxygen production (further reducing power requirements) by not releasing oxygen, for example, when the user is exhaling. Reducing the amount of oxygen produced may effectively reduce the amount of air compression needed for oxygen concentrator 100 (and subsequently may reduce the power demand from the compressors).

Oxygen enriched gas produced by oxygen concentrator 100 is stored in an oxygen accumulator 109 and released to the user as a bolus as the user inhales. The amount of oxygen enriched gas provided by the oxygen concentrator 100 is controlled, in part, by supply valve 160. In an embodiment, supply valve 160 is opened to a sufficient degree and for a sufficient amount of time to provide the appropriate amount of oxygen enriched gas, as estimated by controller 400, to the user.

In an embodiment, pressure sensor 194 may be implemented to determine the onset of inhalation by the user. In use, a conduit 192 for providing oxygen enriched gas is coupled to a user's nose and/or mouth through the airway delivery device 710 and/or mouthpiece 720. At the onset of an inhalation, the user begins to draw air into their body through the nose and/or mouth. As the air is drawn in, a negative pressure is generated at the end of the conduit, due, in part, to the venturi action of the air being drawn across the end of the delivery conduit. Controller 400 may be configured to detect a drop in the pressure signal generated by the pressure sensor 194, the drop indicating the onset of inhalation. Upon detection of the onset of inhalation, supply valve 160 is opened to release a bolus of oxygen enriched gas from the accumulator 109, optionally after first waiting an interval known as the onset delay. A positive change or rise in the pressure indicates an exhalation by the user and is generally a time that release of oxygen enriched gas is discontinued. Generally, when the controller 400 detects a positive pressure change in the pressure signal generated by the pressure sensor 194, valve 160 is closed until the next onset of inhalation. Alternatively, valve 160 may be closed by the controller 400 after a predetermined interval known as the bolus duration. By measuring the intervals between adjacent onsets of inhalation, the controller 400 may estimate the user's breathing rate. By measuring the intervals between onsets of inhalation and the following onsets of exhalation, the controller 400 may estimate the user's inspiratory time.

The amount of the pressure change detected by pressure sensor 194 may be implemented to refine the amount of oxygen enriched gas being provided to the user. For example, if a large negative pressure change is detected by pressure sensor 194, the volume of oxygen enriched gas provided/released to the user may be increased by the controller 400 (through its dynamic control of a supply valve 160) to consider or take into account the increased volume of gas presumably being inhaled by the user. If a smaller negative pressure change is detected, the volume of oxygen enriched gas provided/released to the user may be decreased by the controller 400 (through its dynamic control of a supply valve 160) to take into account the decreased volume of gas presumably being inhaled by the user.

In some embodiments, the sensitivity of the pressure sensor 194 may be affected by the physical distance of the pressure sensor 194 from the user, especially if the pressure sensor is located in oxygen concentrator 100 and the pressure difference is detected through the conduit 192 coupling the oxygen concentrator 100 to the user. In some embodiments, the pressure sensor 194 may be placed in the airway delivery device 710 used to provide the oxygen enriched gas to the user. A signal from the pressure sensor may be provided to controller 400 in the oxygen concentrator 100 electronically via a wire or through telemetry such as through Bluetooth™ or other wireless technology.

A user breathing at a rate of 30 breaths per minute (BPM) during an active state (e.g., walking, exercising, etc.) may consume two and one-half times as much oxygen as a user who is breathing at 12 BPM during an inactive state (e.g., asleep, sitting, etc.). Pressure sensor 194 may be implemented to determine the breathing rate of the user. As described above, controller 400 may process information received from pressure sensor 194 to determine a breathing rate based on the frequency of the onset of inhalation. The detected breathing rate of the user may be applied to adjust the bolus volume of oxygen enriched gas. The bolus volume of the oxygen enriched gas may be increased, kept constant, or decreased as the user's breathing rate increases, as specified by the dose rationing scheme/methodology employed by the oxygen concentrator 100.

Additionally, controller 400 may automatically adjust the bolus volume based on the activity mode of the oxygen concentrator 100.

In some embodiments, if the user's current breathing rate exceeds a predetermined threshold, controller 400 may implement an alarm (e.g., visual and/or audio) to warn the user that the current breathing rate is exceeding the delivery capacity of the oxygen concentrator 100. For example, the threshold may be set at 40 breaths per minute.

In some embodiments, the sensitivity of the oxygen concentrator 100 to pressure changes may be selectively attenuated to reduce false onset of inhalation detections due to movement of air from a different source (e.g., movement of ambient air).

In some embodiments, in active mode, the sensitivity of the oxygen concentrator 100 may be mechanically, electronically, or programmatically attenuated. For example, during active mode, controller 400 may look for a greater pressure drop to indicate the start of a user breath (e.g., an elevated threshold may be compared to the detected pressure drop to determine if the bolus of oxygen should be released). In some embodiments, the pressure sensor 194 may be mechanically altered to be less sensitive to pressure drops. In some embodiments, an electronic signal from the pressure sensor may be electronically altered to be less sensitive to small pressure drops. In some embodiments, during the inactive mode, the sensitivity of the oxygen concentrator 100 may be increased. For example, the controller 400 may look for a smaller pressure drop to indicate the onset of inhalation (e.g., a smaller threshold may be compared to the detected pressure drop to determine if the bolus of oxygen should be released).

Tailoring POD Therapy to a User

In one implementation of pulsed oxygen delivery (POD) therapy as controlled by the methodology of the controller 400, the bolus can be tailored to match the needs of a particular user. The objective may be for an oxygen bolus optimised to the user's breathing pattern, or to maximize alveolar delivery, or both. To do so, an inhalation flow profile may be determined and generated based on information gathered from pressure sensor 194 and/or flow rate sensor 185. An inhalation flow profile is determined/generated based on one or more of the following parameters: the breathing rate of the user; the inhalation volume of the user; the exhalation volume of the user; the peak inspiratory flow rate of the user; and the peak expiratory flow rate of the user. The breathing rate of the user may be estimated by detecting the onsets of inhalation using pressure sensor 194 as previously discussed. Inhalation volume may be estimated by measuring the change in pressure during inhalation (absent any bolus) and calculating or empirically estimating the inhalation volume based on the change in pressure. Exhalation volume may be estimated in a similar manner using positive pressure changes during exhalation. Detection of the end of inhalation may be from the pressure sensor 194. When onset of inhalation is detected using the pressure sensor 194, the onset is characterized by a drop in pressure, relative to ambient. When the pressure begins to increase above ambient, the inhalation is considered complete.

There is a minimum rate of gas exchange necessary to sustain a typical person, which can be expressed as a minimum minute ventilation (e.g., a minimum volume of gas inspired and expired in the course of a minute). Assuming ventilation remains at this minimum minute ventilation, a person who is breathing rapidly is inhaling a lower volume of air in each breath and vice-versa. Hence a minimum tidal volume can be established from the minimum minute ventilation with additional knowledge of breathing rate. By measuring a large population of users, a generic profile of the relative inspiratory flow rate from onset of inhalation to the onset of exhalation may be established/determined. Using the minimum tidal volume and the breathing rate, this generic relative flow rate profile may be adapted mathematically into a minimum inhalation flow profile for a user. This minimum inhalation flow profile (e.g., an inspiratory flow rate versus time representation, such as in data or digital form, that may have a particular shape or curve during inspiration time) can serve as a basis for control parameters that control actuation of a supply valve 160 to release, for delivery, an appropriate or corresponding bolus for the user.

Inhalation flow profile data empirically gathered from a population of users may be evaluated by or used to create an algorithm that determines the appropriate bolus (e.g., volume and shape) based on the estimated minimum inhalation flow profile.

Basing the delivery of oxygen enriched gas on population data and breathing rate might not take into account differences between individual users. For example, people having similar breathing rates can have different inhalation/exhalation volumes, inhalation/exhalation flow rates and, thus, different bolus parameters necessary to produce an appropriate bolus that would more closely correspond to a particular user. A more accurately estimated inhalation flow profile of the user may provide a more accurate basis for control of the bolus of oxygen enriched gas being provided to the user.

Estimating a Delivery Envelope for a User

Figure 7:
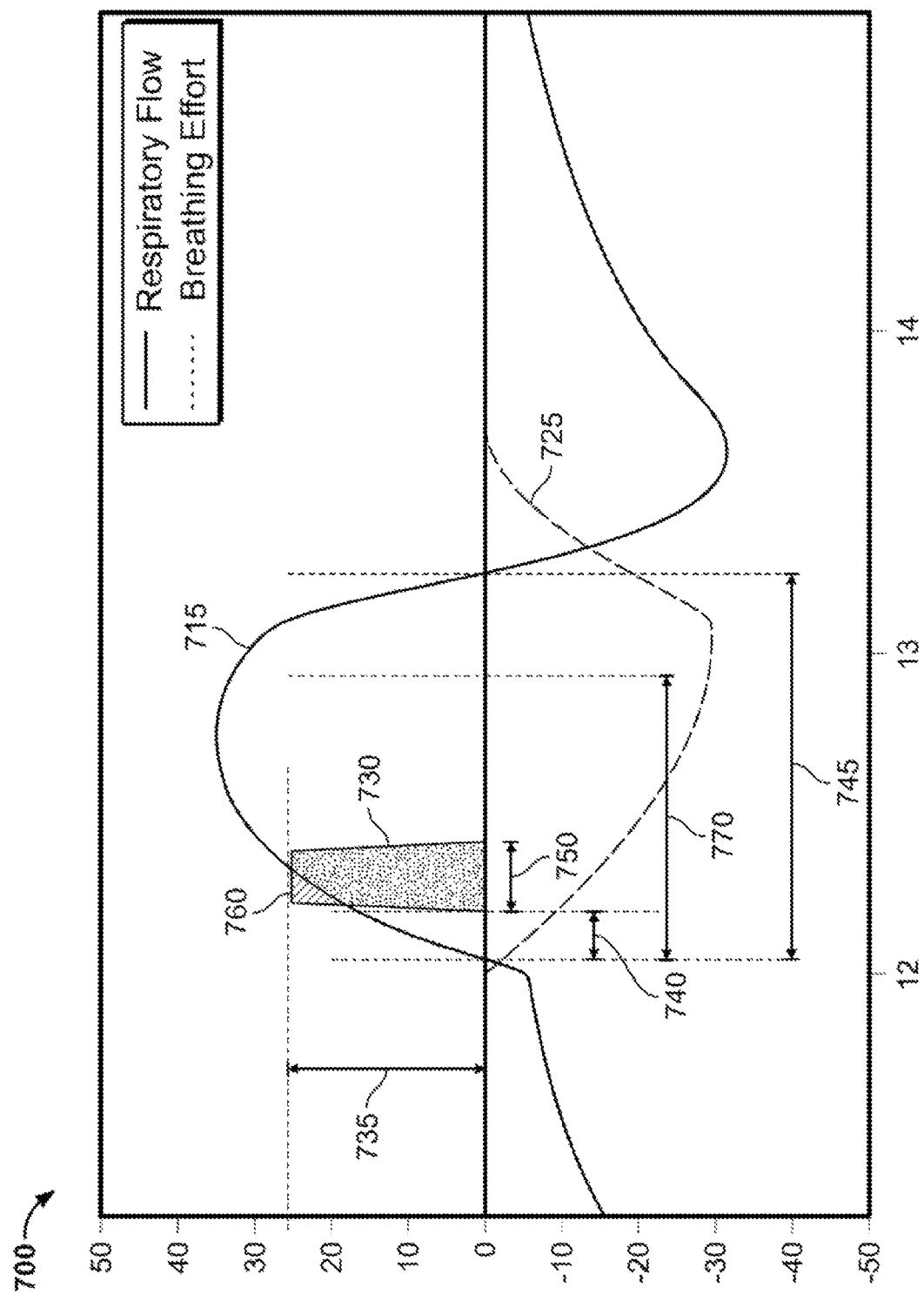
FIG. 7 is a graph illustrating various kinds of waste gas in pulsed oxygen delivery.

FIG. 7 contains a graph 700 illustrating various kinds of waste in POD. The graph 700 contains two traces: trace 715, which represents the respiratory flow rate for a person's breath (positive indicates inspiration) such as determined by a flow rate sensor, and trace 725, which represents respiratory effort (muscular pressure, with negative values indicating inspiratory effort) such as determined by a respiratory effort chest strap type sensor. The interval 745 represents the inspiratory time. The trace 730 represents the amplitude profile of a rectangular bolus of delivered oxygen. (Note that hereinafter, the term "oxygen" is used as shorthand for "oxygen enriched gas", unless its alternative meaning of pure $O_2$ gas is clear from the context.) The parameters of the rectangular bolus are its amplitude 735, its onset delay 740 from the onset of inhalation, and its duration 750. A more general (e.g., non-rectangular) bolus may have a non-constant amplitude profile (amplitude over time), including a profile controlled to match or correspond with an estimate of the user's inhalation flow profile.

The hatched area 760 represents the retrograde flow waste portion of the bolus, i.e. the portion of the bolus whose flow rate exceeds the inspiratory flow rate. The interval 770 represents the "alveolar time" $T_{ALV}$ of the breath, i.e. the interval during which inhaled air reaches the gas-exchanging portion of the lung. After the interval 770, inspired flow only reaches the anatomic deadspace. Any portion of the bolus that lasts beyond the alveolar time $T_{ALV}$ is therefore wasted on anatomic deadspace (anatomic deadspace waste).

For a user with COPD, some portion of the inspired air during the alveolar time $T_{ALV}$, and therefore some portion of the bolus, may also be wasted because it does not reach functioning alveoli. This kind of waste (physiologic deadspace waste) is not illustrated in FIG. 7.

It may be observed from FIG. 7 that the three parameters of a bolus, namely its onset delay, its duration, and its amplitude profile, may vary within certain ranges without incurring retrograde flow or anatomic deadspace waste for a given bolus volume. However, these ranges of variation are interdependent. For example, when a shorter onset delay is chosen, the upper bound on amplitude will need to be lower so that the bolus amplitude profile remains within the area of the user's respiratory flow rate curve that avoids retrograde flow waste or anatomic deadspace waste. Furthermore, for a bolus of predetermined volume, once the amplitude profile is chosen, the duration is fixed also, and vice versa. The interdependence of these parameters, which may serve as control parameters for release of a bolus, may be expressed in a "delivery envelope", a region in parameter space within which the bolus control parameters may be constrained so that the bolus may delivered without incurring retrograde flow waste or anatomic deadspace waste.

The volume of anatomic dead space can be estimated, for example, according to user height or some surrogate dimension (e.g. ulna length, knee-heel distance, etc.). Given this value and the user's estimated inhalation flow profile as previously described, the user's alveolar time $T_{ALV}$ may be estimated, and this value along with the inhalation flow profile itself would provide the interdependent limits on onset delay and amplitude profile for the control of bolus release/generation. The difficulty in estimating the delivery envelope is that a given user's inhalation flow profile is unknown. Although pressure sensor 194 can in theory be calibrated to adequately measure the instantaneous respiratory flow rate (absent any bolus), in practice such calibration cannot be relied upon during POC therapy because (a) during delivery of the bolus the nasal pressure signal is lost, and (b) change in cannula position is routine, so any 'calibration' of a signal from pressure sensor 194 against respiratory flow rate is at best temporary.

However, to estimate a delivery envelope, the user's actual inhalation flow profile is not required. Instead, a 'worst case' might be conservatively assumed, which for pulsed oxygen delivery is that of minimum ventilatory demand for a given user size. On this assumption, anatomic deadspace is maintained while tidal volume is reduced, which is worst case for delivery of the oxygen bolus due to the following conspiring effects:

(a) a longer onset delay (740) due to low inspiratory flows;

(b) the anatomic deadspace occupies an increased proportion of the inspiratory time, such that alveolar time (interval 770) is reduced, and (c) the inhalation flow profile is shallow so the bolus amplitude must be small to avoid retrograde flow waste (area 760).

In overview, a minimum alveolar ventilation may be inferred from a parameter representing the user's body size, e.g. height. Knowing user height also permits estimation of the particular volume portion of the breath that fills the anatomic deadspace. A minimum tidal volume can thus be calculated using the measured breathing rate. Inspiratory duration can be measured as described above, or estimated from the breathing rate, which combined with the minimum tidal volume and a generic relative inhalation profile allows estimation of a minimum inhalation flow profile, i.e. the minimum instantaneous flow rate throughout inspiration. While body size is a preferred user parameter for this purpose, other user parameters may offer similar (but less specific) inference, such as age, weight, sex or combinations thereof. In particular, the use of body size to infer a minimum inhalation flow profile allows the range of users to extend from adult to neonate.

Figure 8:
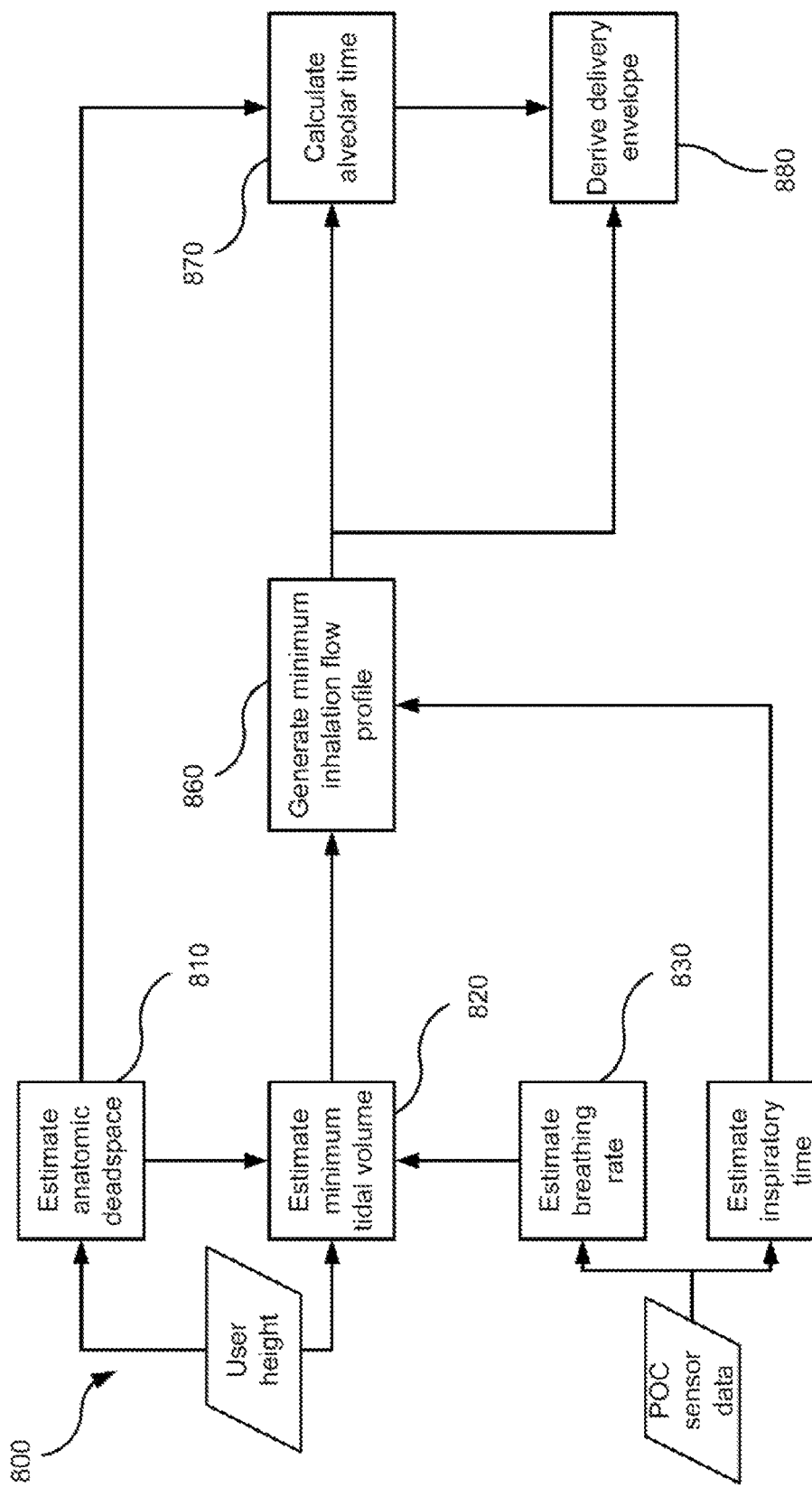
FIG. 8 is a flow chart illustrating a methodology that may be implemented by a processor to estimate a bolus delivery envelope for a user.

FIG. 8 contains a flow chart illustrating a method 800 that may be implemented to estimate the delivery envelope. The method 800 may be implemented by the controller 400, appropriately configured by program instructions stored in memory 420 or a carrier (storage) medium coupled to controller 400, and executed by one or more processors 410 as described above.

The controller 400 may be configured to perform the method 800 only once for a user. Alternatively, the method 800 may be performed repeatedly, for example once per breath, to account for changes in the user's breathing rate and inspiratory time, since these changes will affect the delivery envelope.

The principles underlying the method 800 are:

1. Estimation of the user's anatomic deadspace: Anatomic dead space is approximately correlated to a person's height, and effectively imposes a per-breath augmentation of tidal volume. The method 800 therefore may start at step 810, which estimates the user's anatomic deadspace $VD_{an}$. The estimate may be based on their height. For example, a function may apply a value of height to calculate a value for anatomic deadspace volume or a look-up table may be accessed with the height value to select a corresponding value for anatomic deadspace volume. The user's height (H) may be manually entered/input to the oxygen concentrator 100 via its control panel 600, stored in the memory 420, and accessed by the controller 400. In one implementation, step 810 may implement the formula:

$$VD_{an} = 7.585 \times 10^{-4} \times H(\text{cm})^{2.363} \quad (1)$$

Optionally, a known/measured anatomic deadspace may instead be used/input when available.

2. Estimation of minimum sustainable alveolar ventilation: Mammals possess a minimum resting energy expenditure, also called basal metabolic rate, and in the case of human beings this quantity can be loosely estimated from a person's height (or length for infants). The associated metabolism produces a minimum volume of $CO_2$, i.e. demands a minimum alveolar ventilation. Step 820 therefore makes use of the user's height to estimate the user's minimum alveolar minute ventilation such as by calculation with a function or by look-up table. In one implementation, the user's resting energy expenditure (REE) is estimated from the user's height, and the REE is used to estimate the user's minimum alveolar minute ventilation, $\overset{\&}{V}_{ALV(min)}$.

In one implementation, the user's REE may be estimated from the user's height (e.g., in centimetres) as a piecewise linear interpolation between four breakpoints: H=40, 90, 140, and 190 cm. The corresponding REE values (e.g., in Megajoules per day) at each height breakpoint are as follows:

REE(40 cm)=0.11

REE(90 cm)=3.14

REE(140 cm)=4.82

REE(190 cm)=7.35 (2)

In other implementations, alternative estimates for REE may be made based on other user parameters such as age, weight, and/or sex.

In one implementation, the user's minimum alveolar minute ventilation, $\overset{\&}{V}_{ALV(min)}$ (e.g., in litres per minute) may be estimated from the user's resting energy expenditure (REE) as follows:

$$\overset{\&}{V}_{ALV(min)} = REE \times 29.1 \times \text{ActivityFactor} \times \left(\frac{P_{amb} - 47 \text{ mmHg}}{PACO_2}\right) \quad (3)$$

where $PACO_2$ is the arterial pressure of $CO_2$ in the bloodstream (typically 40 mmHg, but can range as high as 60 mmHg for hypercapnic users), $P_{amb}$ is the ambient pressure (typically 760 mmHg at sea level, with a precise value determined in some implementations by sensing using an ambient pressure sensor on the oxygen concentrator 100). ActivityFactor is an activity factor whose minimum value is unity (one), which when used will give minimum estimates for the user's respiratory parameters such as alveolar minute ventilation, tidal volume, and inhalation flow profile.

The activity factor may be applied to derive different inhalation flow profiles so as to permit its variation in relation to a characterization of the users's respiratory parameters as they may vary such as with respect to activity. A range of values may be implemented as desired. For example, to estimate either "typical" or "elevated" characterizations of the user's respiratory parameters, higher values of the activity factor may be used in equation (3). In such an example, a "typical" inhalation flow profile may be obtained by setting the activity factor to 1.25, and an "elevated" inhalation flow profile suitable for active mode may be obtained by setting the activity factor to 2. The user's activity characterization may be entered or selected as input to the oxygen concentrator 100 via the active mode button 630 or the inactive mode button 635 on control panel 600 and the related value may be appropriately applied to the minimum alveolar minute ventilation determination.

A variant of equation (3) may include a further multiplying factor, PathologyFactor, which may take on different non-unity values associated with different pathologies, such as COPD, OHS, NMD, etc. The user's pathology may be entered as a manual setting to the oxygen concentrator 100 via its control panel 600, and converted to a pathology factor, e.g. via a lookup table stored in the memory 420. For example, COPD may be associated with a pathology factor of 1.25, with the result that the minimum, typical, and elevated estimates of alveolar minute ventilation will be 25% greater than those of a healthy person.

Figure 10A:
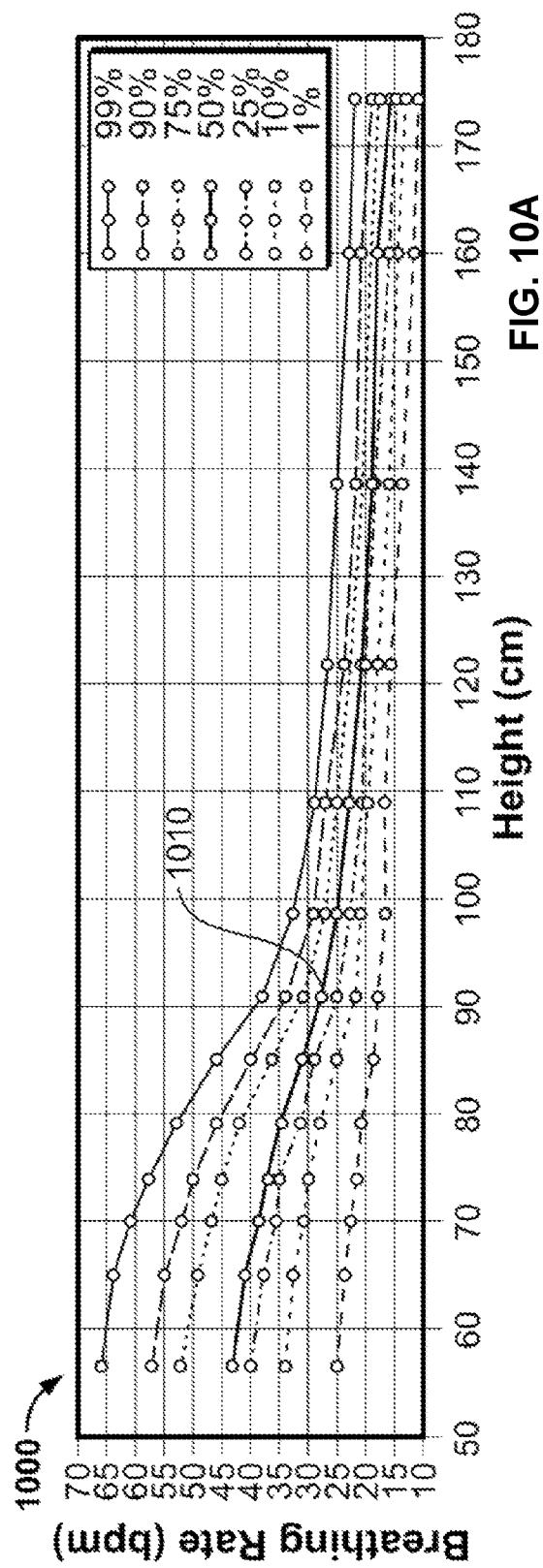
FIG. 10A is a graph illustrating a range of breathing rates for a range of heights from 50 to 180 centimetres derived from population age-rate data.

3. Knowledge of breathing rate: Prior to therapy commencement, breathing rate may be initialized from determined and stored values from one or more prior sessions or estimated from the user's height using population data. For example, FIG. 10A contains a graph 1000 illustrating a range of breathing rates for a range of heights from 50 to 180 centimetres derived from population age-rate data. The middle trace 1010 represents the median breathing rate as a function of height. Thus, age and/or height data may be entered or selected as input to the oxygen concentrator 100 via its control panel 600 and the values may be applied to a look-up table or function representing any of the curves illustrated by the graph 1000 (e.g., median breathing rate at trace 1010) for determination of breathing rate by the controller 400. During therapy, step 830 may use POC sensor data, e.g. from the pressure sensor 194, to estimate the user's breathing rate BR as described above.

4. Estimation of minimum tidal volume: Step 820 estimates the user's minimum tidal volume $V_{T(min)}$ from the user's minimum alveolar minute ventilation, $\overset{\&}{V}_{ALV(min)}$, the user's breathing rate BR, and the anatomic deadspace $VD_{an}$. For example, the controller 400 may determine minimum tidal volume $V_{T(min)}$ by applying the following equation:

$$V_{T(min)} = VD_{an} + \frac{\overset{\&}{V}_{ALV(min)}}{BR} \quad (4)$$

Optionally, the user's minimum minute ventilation may be estimated as the product of the user's minimum tidal volume $V_{T(min)}$ and the user's breathing rate BR, or as the sum of the product of the user's anatomic deadspace $VD_{an}$ and the user's breathing rate BR, and the user's minimum alveolar minute ventilation, $V_{ALV(min)}$&.

5. Estimation of inspiratory time: The user's inspiratory time may be estimated from the pressure signal as described above. Step 840 in one implementation therefore processes data from the pressure sensor 194 to estimate the user's inspiratory time $T_I$ as described above.

Figure 10B:
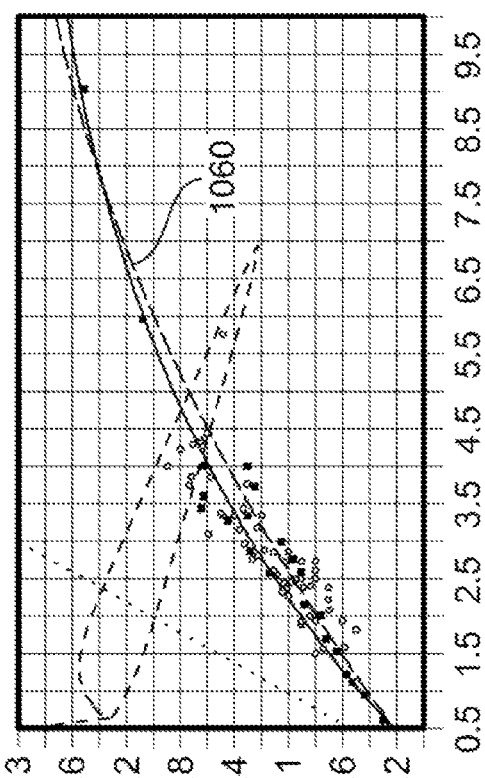
FIG. 10B is a graph illustrating a range of inspiratory times for a range of breath periods from 0.5 to 10 seconds obtained from published clinical data.

In an alternative implementation, step 840 uses published clinical data to obtain inspiratory time $T_I$ from the user's height. For example, the controller 400 in step 840 may first obtain an estimate of breathing rate from user height by applying a function or look-up table representing data of the trace 1010 of the graph 1000 of FIG. 10A. The controller 400 in step 840 may then apply a function or look-up table representing data in the curve 1060 in the graph 1050 in FIG. 10B (obtained from published clinical data) to obtain the inspiratory time $T_I$ from the breath period (reciprocal of breathing rate in breaths per second).

6. Estimation of the flow profile of the average inspiration: The shape of the relative inhalation flow profile of a spontaneously breathing user can be approximated by a template function q(t) that rises from 0 to 1 and returns to 0 over the interval [0, 1]. The controller 400 may fit this template function to a user's minimum tidal volume $V_{T(min)}$ and inspiratory time $T_I$ to generate a minimum inhalation flow profile $Q_{in(min)}(t)$ for the user.

Step 860 therefore fits a template function q(t) to the minimum tidal volume $V_{T(min)}$ and inspiratory time $T_I$ of the user to generate the user's minimum inhalation flow profile $Q_{in(min)}(t)$, which takes the form $$Q_{peak} q\left(\frac{t}{T_I}\right)$$

where $Q_{peak}$ is the amplitude or peak value to be fitted. Step 860 determines the peak flow rate $Q_{peak}$ using the following definition of tidal volume:

$$V_{T(min)} = \int_0^{T_I} Q_{peak} q\left(\frac{t}{T_I}\right) dt \quad (5)$$

In one implementation of step 860, the template function q(t) is a sinusoidal half-wave (q(t)=sin(πt)), so the minimum inhalation flow profile $Q_{in(min)}(t)$ takes the form of a sinusoidal half-wave of peak value $Q_{peak}$ and duration equal to the inspiratory time $T_I$ as follows:

$$Q_{in(min)}(t) = Q_{peak} \sin\left(\frac{\pi t}{T_I}\right), \ 0 \le t \le T_I \quad (6)$$

The peak value $Q_{peak}$ of the sinusoidal minimum inhalation flow profile $Q_{in(min)}(t)$ is related to the minimum tidal volume $V_{T(min)}$ via the following formula:

$$Q_{peak} = \frac{\pi}{2} \frac{V_{T(min)}}{T_I} \quad (7)$$

In other implementations, other template functions q(t) may be used to generate the minimum inhalation flow profile $Q_{in(min)}(t)$, e.g. a raised cosine (squared sine), parabola, root sine, or sine to the power of 0.7. In such implementations there will be a different relationship between the peak value $Q_{peak}$ of the minimum inhalation flow profile and the minimum tidal volume $V_{T(min)}$, derivable from equation (5).

7. Calculation of an alveolar time for the minimum sustainable tidal volume: At step 870, the controller 400 uses the user's anatomic deadspace $VD_{an}$ estimated at step 810 and the minimum inhalation flow profile $Q_{in(min)}(t)$ of the user generated at step 860 to calculate the user's alveolar time $T_{ALV}$. Step 870 uses the following relation:

$$VD_{an} = \int_{T_{ALV}}^{T_I} Q_{in(min)}(t) dt \quad (8)$$

8. Calculation of a delivery envelope: The delivery envelope is determined in accordance with the minimum inhalation flow profile $Q_{in(min)}(t)$ so that the bolus is bounded (e.g. in amplitude and time) by the onset of inhalation and the estimated alveolar time $T_{ALV}$ as indicated by the profile.

For example, at step 880 the controller 400 derives the delivery envelope of the user based on the user's minimum inhalation flow profile $Q_{in(min)}(t)$ and the alveolar time $T_{ALV}$ of the user. The delivery envelope is a set of constraints on the bolus parameters based on the alveolar time $T_{ALV}$ calculated at step 870 and the minimum inhalation flow profile $Q_{in(min)}(t)$ calculated at step 860. The constraints are imposed by the avoidance of retrograde flow waste and anatomic deadspace waste of the bolus volume. The constraints are:

$$0 \le Q_b(t) \le Q_{in(min)}(t), \quad t \in [t_D, t_D + t_B] \quad (9)$$
$$Q_b(t) = 0 \quad \text{elsewhere}$$

$$t_D + t_B \le T_{ALV} \quad (10)$$

where $t_D$ is the onset delay of the bolus, $t_B$ is the bolus duration, and $Q_b(t)$ is the bolus amplitude profile. In some versions, one or more of the constraints (8, 9, 10) may be in the form of processing rules for operation of the controller in relation to controlling bolus release as described in more detail herein.

Delivering POD Therapy Based on the Delivery Envelope

Figure 9:
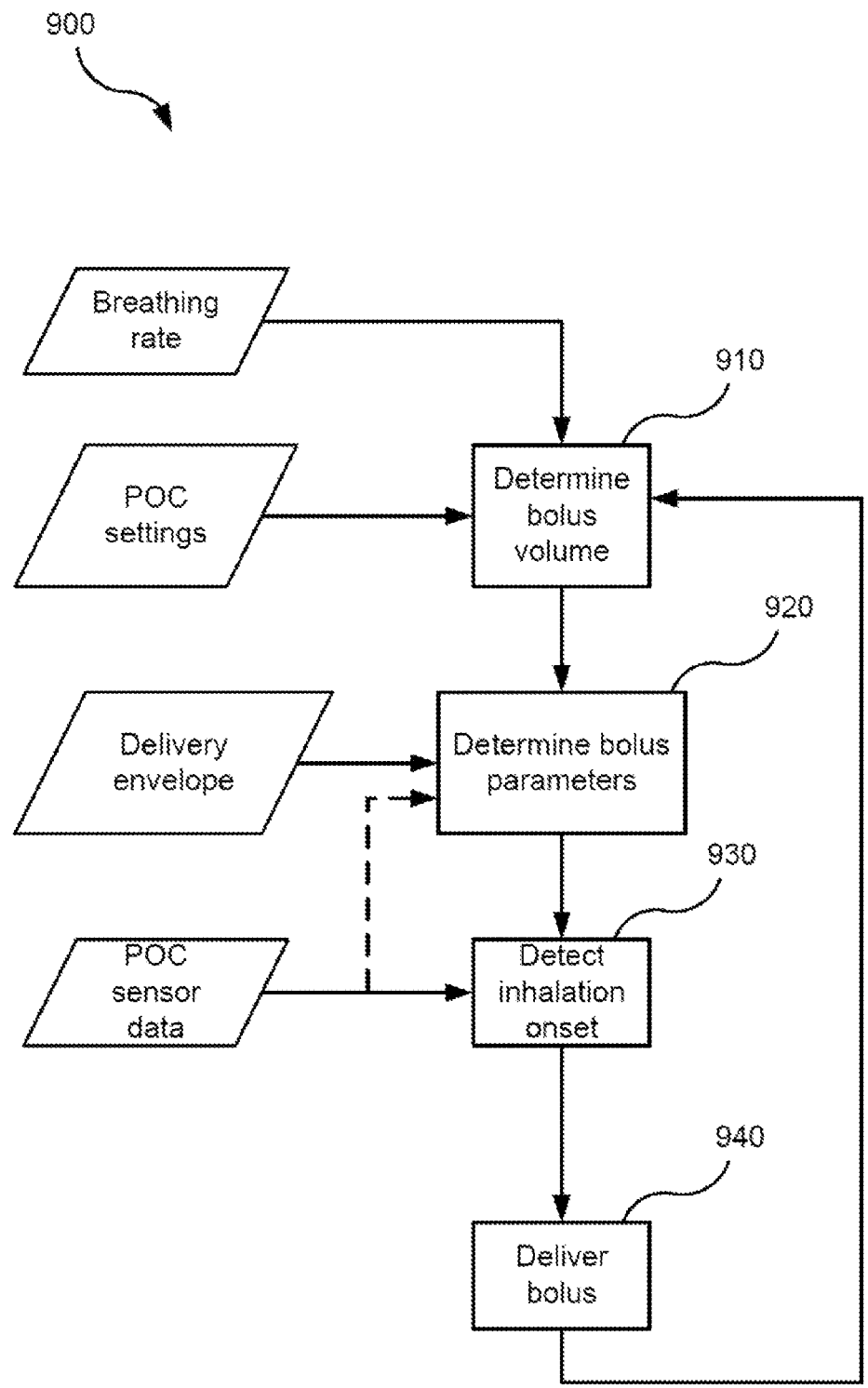
FIG. 9 is a flow chart illustrating a methodology that may be implemented by a processor to control delivery of a bolus within the bolus delivery envelope estimated using the method of FIG. 8.

Once a delivery envelope is determined for a user, POD therapy may be delivered to the user based on the delivery envelope. FIG. 9 contains a flow chart illustrating a method 900 for valve control over oxygen release that may be used to deliver the POD therapy. The method 900 may be implemented by the controller 400, appropriately configured by program instructions stored in memory 420 or a carrier medium coupled to controller 400, and executed by one or more processors 410 as described above, for control of one or more supply valves (e.g., supply valve 160).

The method 900 is represented as a loop, each iteration of which corresponds to a breath. The methods 800 and 900 may run substantially in parallel, so that the delivery envelope used by the method 900 is repeatedly updated by the method 800 as the user's breathing rate and inspiratory time change.

The method 900 may start at step 910, which applies the breathing rate estimated at step 830 and one or more settings of the oxygen concentrator 100 to determine a bolus volume for the POD therapy. The determination at step 910 may implement a predetermined dose rationing scheme that sets out how the bolus volume varies with breathing rate and settings of the oxygen concentrator 100, in particular the prescribed continuous flow rate set by the dosage buttons 620 to 626 on the control panel 600.

In one example of a dose rationing scheme, the bolus volume remains fixed with breathing rate, but varies in proportion to the prescribed continuous flow rate set by the dosage buttons 620 to 626. As described above, in one implementation the bolus volume may be set to 11 mL for each LPM of prescribed continuous flow rate. Fixed bolus volume schemes tend to produce a more constant fraction of inspired oxygen ($FiO_2$) if tidal volume is approximately preserved as breathing rate changes.

In another example of a dose rationing scheme, the bolus volume is varied in inverse proportion to the breathing rate, as well as in proportion to the prescribed continuous flow rate. So, for example, the bolus volume determined by step 910 at 40 BPM would be half the bolus volume at 20 BPM for a given prescribed continuous flow rate. Under this scheme, the average flow rate (minute volume) of oxygen remains fixed with breathing rate. The oxygen delivered might not keep up with increasing ventilation requirements, and users might expect to use a higher continuous-flow-rate setting for exercise to avoid a drop in FiO2.

Yet another example of a dose rationing scheme is a hybrid fixed bolus volume/fixed minute volume scheme. Such a scheme may deliver fixed bolus volumes at low breathing rates reverting to a fixed minute volume of oxygen scheme when the maximum oxygen output (minute volume) of the oxygen concentrator 100 is reached.

In one implementation, the oxygen concentrator 100 may be configured to switch from a fixed minute volume dose rationing scheme to a fixed bolus volume dose rationing scheme, possibly with a higher bolus volume than currently being provided, on activation of a 'boost' control on the control panel 600 of the oxygen concentrator 100. A user might activate such a control, for example, prior to commencing exercise. The oxygen concentrator 100 may be configured to switch back from the fixed bolus volume dose rationing scheme to the fixed minute volume dose rationing scheme either after a predetermined interval or on de-activation of the 'boost' control. For example, in response to receiving a boost signal from an input interface (e.g., a boost button) of the oxygen concentrator, the controller of the oxygen concentrator may control release of one or more boost boluses. The total volume of oxygen enriched gas of each released boost bolus of the one or more boost boluses may include an equivalent volume that satisfies a continuous-flow-rate setting of the oxygen concentrator as set at the input interface plus an additional volume quantity of oxygen enriched gas.

Step 920 follows, which uses the bolus volume calculated at step 910, the current delivery envelope as determined by the method 800, and (optionally) the POC sensor data to determine the bolus parameters. One or more implementations of step 920 are described below.

At the next step 930, the controller 400 awaits the onset of inhalation, which may be detected from the POC sensor data as described above. Finally, at step 940, the bolus is delivered according to the bolus parameters determined at step 920. The delivery of the bolus according to the bolus parameters is achieved by generating one or more bolus release control signals to actuate the supply valve 160 as described above, such as in accordance with timing and amplitude profile to satisfy the determined delivery envelope.

The method 900 then returns to step 910 to calculate the volume of the bolus for the next breath.

In an alternative implementation, the bolus volume is only computed once, so the method 900 returns to step 920 rather than step 910. In a further alternative implementation, the bolus parameters are only computed once, so the method 900 returns to step 930 rather than step 910.

Determination of Bolus Parameters Based on the Delivery Envelope

In relation to the controller 400 generating a bolus release control signal at step 940 to achieve a given bolus volume VB, the bolus amplitude profile $Q_b(t)$ must satisfy the volume constraint:

$$\int_0^{T_I} Q_b(t)dt = V_B \quad (11)$$

Any strategy to choose the onset delay $t_D$, the bolus duration $t_B$, and the bolus amplitude profile $Q_b(t)$ within the delivery envelope (constraints (9) to (10)) and subject to the volume constraint (11) may be used at step 920.

In one example, the bolus amplitude profile $Q_b(t)$ follows the minimum inhalation flow profile $Q_{in(min)}(t)$ within the range $[t_D, t_D+t_B]$, and is zero outside that range, which satisfies constraint (9). An onset delay $t_D$ may be chosen subject to constraint (10); then applying the volume constraint (11) fixes the bolus duration $t_B$. If the bolus duration $t_B$ does not satisfy constraint (10), a lower onset delay $t_D$ must be chosen and the process repeated until both the onset delay $t_D$ and the bolus duration $t_B$ satisfy constraint (10). Alternatively, a bolus duration $t_B$ may be chosen subject to constraint (10); then applying the volume constraint (11) fixes the onset delay $t_D$. If the onset delay $t_D$ does not satisfy constraint (10), a longer bolus duration $t_B$ must be chosen and the process repeated until both the onset delay $t_D$ and the bolus duration $t_B$ satisfy constraint (10).

In another example, the bolus amplitude profile $Q_b(t)$ is constant with a value of $Q_{in(min)}(t_D)$ within the range $[t_D, t_D+t_B]$, and zero outside that range, which satisfies constraint (9). A similar process to that described above of choosing an onset delay $t_D$ subject to constraint (10) and applying the volume constraint (11) to fix the bolus duration $t_B$, or vice versa, may be followed.

Figure 11:
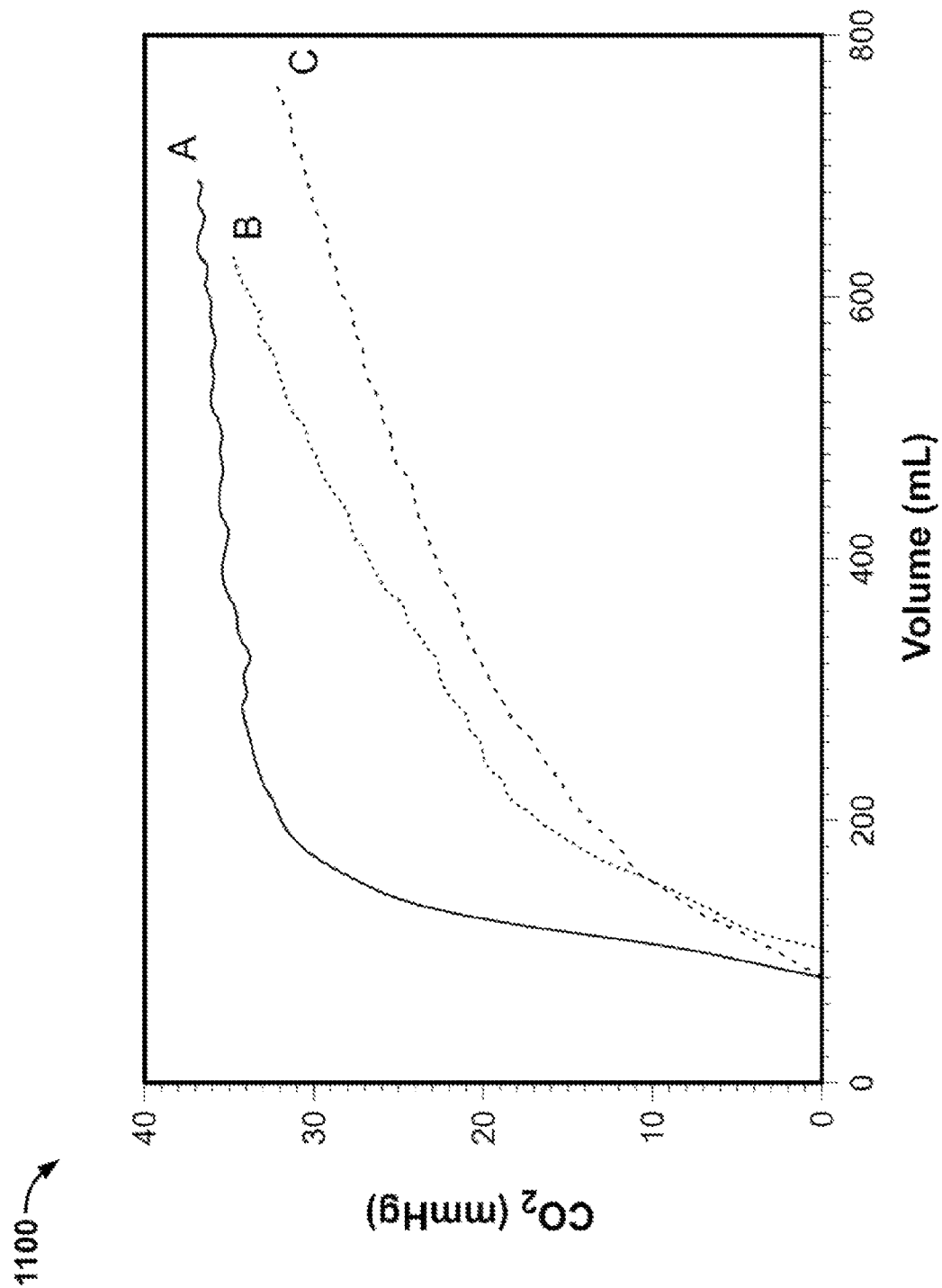
FIG. 11 is a graph showing three representative volume capnograms (partial pressure of exhaled $CO_2$ plotted against exhaled volume) from different user groups.

In general, once the bolus amplitude profile $Q_b(t)$ is chosen, there is one degree of bolus timing freedom within the delivery envelope, i.e. the choice of bolus duration $t_B$ determines the onset delay $t_D$, or vice versa. The timing freedom is maximised if the bolus amplitude is as high as possible within the delivery envelope, which means bolus duration $t_B$ is minimised. That degree of freedom may be utilised to optimise the bolus timing over multiple breaths, so as to maximise the beneficial effect of the bolus. Each successive iteration of step 920 may choose a different bolus timing within the delivery envelope. The beneficial effect on the user of each bolus timing may be estimated, either subjectively by feedback from the user, via a user control on the control panel 600, or objectively via a POC sensor that is connected to the user (the optional input to step 920). One example of objective estimation is via an oxygen saturation sensor on the user's finger, with a larger value of oxygen saturation indicating a more beneficial effect. Another example of objective estimation may be via mainstream volume capnography waveform analysis of the user's exhalate. This may allow inference of optimal timing for an oxygen bolus release during inspiration. The capnogram's Phase 3 slope and fluctuations in slope throughout exhalation provide coarse information on the efficiency of gas exchange progressively within the lung, which may be informative (in reverse) during inspiration. FIG. 11 contains a graph 1100 showing three representative volume capnograms (partial pressure of exhaled $CO_2$ plotted against exhaled volume) from different user groups. Trace A is from healthy individuals, Trace B from an airway diseases group, and Trace C from an emphysema group. The different shapes, in particular the slope at the end of exhalation, indicate different dynamics of gas exchange throughout the breath. Similar information might be inferred using sidestream capnogram monitoring, a technology suitable for incorporating into an oxygen concentrator such as the oxygen concentrator 100.

By such measures, an optimisation strategy may guide the choice of bolus timing at the next iteration of step 920 so as to converge on a bolus timing that achieves the most beneficial effect. For example, such feedback may be implemented by the controller 400 to make incremental adjustments to the bolus timing within the constraints previously described within a use session or over multiple use sessions so as to improve the subjective feedback (e.g., user comfort) and/or objective feedback (saturation data). The controller 400 may then settle on a bolus timing when such feedback obtains an optimum level. In this fashion, the third kind of waste, physiologic deadspace waste, may be effectively minimised, as the bolus timing that provides the most beneficial effect is the bolus timing that allows the bolus to reach the greatest number of functioning alveoli, i.e. that minimises physiologic deadspace waste.

Other considerations that may be implemented by a controller 400 in setting of bolus parameters within the delivery envelope may include:
  User comfort: Discomfort within the nares may be associated with an abruptly rising bolus. A softness setting via a user 'softness' control may alter the initial rate of rise of bolus amplitude, thereby affecting the duration of the bolus according to the volume constraint (11).
  Power consumption: if high delivery pressures invoke higher power consumption, an 'economy mode' may be offered, such as when operating from batteries, in which the bolus duration is maximized such that delivery pressure and hence power consumption are minimized.
  Acoustic noise (e.g. operation during sleep or school): if lower bolus amplitudes offer acoustic noise reduction, the bolus duration may be maximised such that the bolus amplitude and hence acoustic noise are minimised.

Other Applications of the Inhalation Flow Profile

Although the inhalation flow profile and the other user-size-derived respiratory parameter estimates described above have particular benefits to oxygen concentrator POD therapy algorithms and system design optimisation, they may also have application to respiratory therapies other than PODs and respiratory therapy devices other than oxygen concentrators. User-specific estimates of minimum, typical, or elevated minute ventilation, tidal volume, anatomic deadspace, peak inspiratory flow rate, and inhalation flow profile can assist pre-configuration or control of a respiratory therapy device in a manner that is tailored to the user. Some examples are:

Initialising tidal volume during volume control ventilation in acute applications: It is recommended practice of modern acute ventilation to minimize tidal volume (protective ventilation), in order to reduce the possibility of ventilator-induced lung injury. In doing so, minimising tidal volumes takes precedence over normalising $CO_2$ (permissive hypercapnia). In this context the use of a minimum tidal volume calculated from resting energy expenditure/basal metabolic rate is well suited.
  Initialising trigger sensitivity based on the minimum peak inspiratory flow rate.
  Initialising low or high tidal volume alarms based on the minimum or elevated tidal volume respectively.
  Initialising low or high minute ventilation alarms based on the minimum or elevated minute ventilation respectively.
  Initialising target tidal volume settings for volume assurance modes using the typical tidal volume for a given pathology.
  Assisting remote management of users on therapy, for instance detection of hypoventilation using the minimum minute ventilation.
  Adapting internal behaviors of sophisticated ventilation algorithms. For example:
    When initiating users on nocturnal ventilation therapies, it may be advantageous to reach the final therapy target progressively, to permit the user to gradually acclimatize to respiratory pressure therapy. The height-based minimum ventilation estimates can determine a target minute ventilation automatically, through knowledge of the user's height, initial $PaCO_2$ and target $PaCO_2$. Thus, a device's pressure support, volume or ventilation target can be adjusted over multiple days or weeks to reach the final clinical target for the therapy.
    Automatic EPAP adjustment schemes typically respond to hypopneas, usually judged relative to surrounding breaths. A height-based minimum tidal volume estimate can be implemented as an absolute reference, rather than just a relative measure for judging hypopneas.

General Remarks

In the present disclosure, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims. For example, although the methodologies for valve control of oxygen release are implemented in relation to a POC, they may also be implemented with other devices, such as a high flow therapy device or a respiratory pressure therapy device (e.g., ventilator, CPAP or PAP) that may employ use of supplemental oxygen such with a POC or oxygen source.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

LABEL LIST oxygen concentrator 100
inlets 101
air inlet 106
inlet muffler 108
accumulator 109
valves 122
valves 124
concentrator outlet 130
valves 132
outlet muffler 133
valves 134
check valves 142
check valves 144
flow restrictors 151
valves 152
flow restrictors 153
valve 154
flow restrictors 155
supply valve 160
expansion chamber 162
ultrasonic sensor system 165
emitters 166
receiver 168
outer housing 170
outlet 172
outlet port 174
small orifice flow restrictor 175
power supply 180
flow rate sensor 185
filter 187
connector 190
conduit 192
pressure sensor 194
compression system 200
compressor 210
compressor outlet 212
motor 220
external armature 230
air transfer device 240
compressor outlet conduit 250
canister system 300
canister 302
canister 304
base 315
outlet 325
gases 327
controller 400
processor 410
memory 420
control panel 600
input port 605
power button 610
button 620 button 622
button 624
button 626
button 630
button 635
altitude button 640
battery check button 650
relative battery power remaining LED 655
graph 700
airway delivery device 710
trace 715
mouthpiece 720
trace 725
trace 730
amplitude 735
onset delay 740
inspiratory time 745
duration 750
potential waste 760
interval 770
method 800
step 830
step 840
step 860
step 870
step 880
method 900
step 910
step 920
step 930
step 940
graph 1000
trace 1010
graph 1050
curve 1060
graph 1100

What is claimed is:

1. A method of controlling oxygen enriched gas release with a controller of an oxygen concentrator, the method comprising:
generating a minimum inhalation flow profile of a user based on a size parameter of the user;
determining one or more control parameters characterizing a bolus of oxygen enriched gas based on the generated minimum inhalation flow profile; and
generating, with the controller, a bolus release control signal for controlling release of a bolus of oxygen enriched gas according to the determined one or more control parameters.

2. The method of claim 1, further comprising calculating an alveolar time for the user based on the minimum inhalation flow profile, wherein the one or more control parameters are further based on the calculated alveolar time.

3. The method of claim 1, further comprising deriving a delivery envelope for the one or more control parameters from the minimum inhalation flow profile, and constraining the one or more control parameters within the delivery envelope.

4. The method of claim 3, further comprising calculating an alveolar time for the user based on the minimum inhalation flow profile, wherein the delivery envelope is further based on the calculated alveolar time.

5. The method of claim 2, wherein the size parameter of the user is height, further comprising estimating an anatomic deadspace of the user from the height, wherein the alveolar time is further based on the estimated anatomic deadspace.

6. The method of claim 1, further comprising generating one or more sensor signals representing properties of the oxygen concentrator or the user.

7. The method of claim 6, further comprising estimating an inspiratory time of the user from the one or more sensor signals.

8. The method of claim 7, wherein the minimum inhalation flow profile is further based on the estimated inspiratory time.

9. The method of claim 1, further comprising determining a volume for the bolus based on a setting of the oxygen concentrator, wherein the one or more control parameters are further based on the determined volume for the bolus.

10. The method of claim 9, wherein the determining the volume for the bolus is further based on a breathing rate of the user.

11. The method of claim 10, further comprising estimating the breathing rate of the user from one or more sensor signals representing properties of the oxygen concentrator or the user.

12. The method of claim 9, wherein the determining the one or more control parameters comprises:
setting an onset delay that is less than an inspiratory time of the minimum inhalation flow profile;
setting a bolus amplitude profile to correspond with the minimum inhalation flow profile between the onset delay and a bolus duration; and
computing the bolus duration based on the bolus amplitude profile and the determined volume for the bolus.

13. The method of claim 9, wherein the determining the one or more control parameters comprises:
setting an onset delay that is less than an inspiratory time of the minimum inhalation flow profile;
setting a bolus amplitude profile to be equal to a value of the minimum inhalation flow profile at the onset delay over a range from the onset delay to a bolus duration; and
computing the bolus duration based on the bolus amplitude profile and the determined volume for the bolus.

14. The method of claim 12, further comprising calculating an alveolar time for the user based on the minimum inhalation flow profile, wherein the onset delay is less than the calculated alveolar time.

15. The method of claim 14, wherein the size parameter is a height of the user, further comprising estimating an anatomic deadspace of the user from the height of the user, wherein the calculated alveolar time is further based on the estimated anatomic deadspace.

16. The method of claim 9, wherein the determining the one or more control parameters comprises:
setting a bolus duration that is less than an inspiratory time of the minimum inhalation flow profile;
setting a bolus amplitude profile to follow the minimum inhalation flow profile between an onset delay and the bolus duration; and
computing the onset delay based on the bolus amplitude profile and the determined volume for the bolus.

17. The method of claim 9, wherein the determining the one or more control parameters comprises:
setting a bolus duration that is less than an inspiratory time of the minimum inhalation flow profile;
setting a bolus amplitude profile to be equal to a value of the minimum inhalation flow profile at an onset delay over a range from the onset delay to the bolus duration; and
computing the onset delay based on the bolus amplitude profile and the determined volume for the bolus.

18. The method of claim 16, further comprising calculating an alveolar time for the user based on the minimum inhalation flow profile, wherein the bolus duration is less than the alveolar time.

19. The method of claim 18, wherein the size parameter is a height of the user, further comprising estimating an anatomic deadspace of the user from the height of the user, wherein the alveolar time is further based on the anatomic deadspace.

20. The method of claim 1, further comprising:
estimating a beneficial effect of a bolus delivered in accordance with the bolus release control signal;
determining one or more further control parameters characterizing an additional bolus of oxygen enriched gas based on the minimum inhalation flow profile and the estimated beneficial effect; and
generating, with the controller, a further bolus release control signal according to the determined one or more further control parameters.

21. The method of claim 1, further comprising receiving, in the controller, a boost signal from an input interface of the oxygen concentrator, and in response thereto, controlling, by the controller of the oxygen concentrator, release of one or more boost boluses, wherein a total volume of oxygen enriched gas of a released bolus of the one or more boost boluses includes (1) an equivalent volume that satisfies a continuous-flow-rate setting of the oxygen concentrator as set at the input interface plus (2) an additional volume quantity of oxygen enriched gas.

22. The method of claim 21, wherein the controller discontinues release of the additional volume quantity of oxygen enriched gas after a predetermined time or in response to a further signal from the input interface of the oxygen concentrator.

23. The method of claim 1, wherein the determining the one or more control parameters comprises calculating the control parameters to reduce one or more of retrograde flow waste, anatomic deadspace waste and physiologic deadspace waste.

24. The method of claim 1, further comprising releasing a bolus of oxygen enriched gas in accordance with the bolus release control signal for delivery to the user via a delivery device, whereby the delivered bolus reduces one or more of retrograde flow waste, anatomic deadspace waste and physiologic deadspace waste.

25. An oxygen concentrator apparatus comprising:
at least two canisters;
gas separation adsorbent disposed in the at least two canisters, wherein the gas separation adsorbent separates at least some nitrogen from air in the at least two canisters to produce oxygen enriched gas;
a compression system, the compression system comprising:
a compressor coupled to at least one of the canisters, wherein the compressor compresses air during operation; and
a motor coupled to the compressor, wherein the motor drives operation of the compressor;
an accumulator coupled to one or more of the canisters, wherein oxygen enriched gas produced in one or more of the canisters is passed into the accumulator during use; and
a controller, including one or more processors, and a set of valves coupled to the controller, the controller configured to control operation of the set of valves to (a) produce oxygen enriched gas into the accumulator and (b) release the produced oxygen enriched gas from the accumulator in at least one bolus, the controller further configured to:
generate a minimum inhalation flow profile of a user based on a size parameter of the user;
determine one or more control parameters characterizing the at least one bolus based on the generated minimum inhalation flow profile; and
generate a bolus release control signal according to the determined one or more control parameters, the generated bolus release control signal configured to cause the at least one bolus to be released from the accumulator.

26. The oxygen concentrator apparatus of claim 25, further comprising a control panel coupled to the controller and configured to receive the size parameter of the user via manual entry.

27. The oxygen concentrator apparatus of claim 25 wherein the controller comprises a carrier medium having processor control instructions that, when executed by the one or more processors, cause the oxygen concentrator apparatus to perform the method of claim 1.

28. An oxygen concentrator apparatus comprising:
at least two canisters;
gas separation adsorbent disposed in the at least two canisters, wherein the gas separation adsorbent separates at least some nitrogen from air in the at least two canisters to produce oxygen enriched gas;
a compression system, the compression system comprising:
a compressor coupled to at least one of the canisters, wherein the compressor compresses air during operation; and
a motor coupled to the compressor, wherein the motor drives operation of the compressor;
an accumulator coupled to one or more of the canisters, wherein oxygen enriched gas produced in one or more of the canisters is passed into the accumulator during use; and
a controller, including one or more processors, and a set of valves coupled to the controller, the controller configured to control operation of the set of valves to (a) produce oxygen enriched gas into the accumulator and (b) release, in pulsed oxygen delivery mode, the produced oxygen enriched gas from the accumulator in at least one bolus, the controller further configured to:
derive a delivery envelope of parameters of a potential bolus of oxygen enriched gas based on a size parameter of a user;
determine one or more control parameters characterizing a deliverable bolus of oxygen enriched gas so that the one or more parameters are constrained within the delivery envelope; and
generate a bolus release control signal according to the determined one or more control parameters, the bolus release control signal for controlling release of a bolus of oxygen enriched gas from the accumulator.

29. An oxygen concentrator apparatus comprising:
at least two canisters;
gas separation adsorbent disposed in the at least two canisters, wherein the gas separation adsorbent separates at least some nitrogen from air in the at least two canisters to produce oxygen enriched gas;
a compression system, the compression system comprising:

a compressor coupled to at least one of the canisters, wherein the compressor compresses air during operation; and a motor coupled to the compressor, wherein the motor drives operation of the compressor;

an accumulator coupled to one or more of the canisters, wherein oxygen enriched gas produced in one or more of the canisters is passed into the accumulator during use; and a controller, including one or more processors, and a set of valves coupled to the controller, the controller configured to control operation of the set of valves to (a) produce oxygen enriched gas into the accumulator and (b) release the produced oxygen enriched gas from the accumulator, the controller further configured to:

estimate a tidal volume for a user based on a size parameter of the user and a breathing rate of the user; and generate an inhalation flow profile for the user from the tidal volume and an inspiratory time for the user.

30. A respiratory therapy apparatus comprising:

a controller, including one or more processors, configured to control one or more operations of the respiratory therapy apparatus to produce a respiratory therapy, wherein the controller is configured to:

estimate a resting energy expenditure of a user based on a size parameter of the user;

estimate a respiratory parameter for the user based on the estimated resting energy expenditure; and control an operation of the respiratory therapy apparatus based on the estimated respiratory parameter.

* * * * *